US009649084B2

(12) United States Patent
Kim

(10) Patent No.: US 9,649,084 B2
(45) Date of Patent: May 16, 2017

(54) X-RAY IMAGING APPARATUS AND METHOD FOR CREATING X-RAY IMAGE

(71) Applicant: Samsung Electronics Co., Ltd., Suwon-si, Gyeonggi-do (KR)

(72) Inventor: Myeong Je Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 118 days.

(21) Appl. No.: 14/804,402

(22) Filed: Jul. 21, 2015

(65) Prior Publication Data
US 2016/0015353 A1    Jan. 21, 2016

(30) Foreign Application Priority Data

Jul. 21, 2014  (KR) .................. 10-2014-0091732
Apr. 29, 2015  (KR) .................. 10-2015-0060383

(51) Int. Cl.
*A61B 6/00*  (2006.01)
*A61B 6/04*  (2006.01)

(52) U.S. Cl.
CPC ............. *A61B 6/544* (2013.01); *A61B 6/405* (2013.01); *A61B 6/4452* (2013.01); *A61B 6/4464* (2013.01); *A61B 6/482* (2013.01); *A61B 6/54* (2013.01); *A61B 6/542* (2013.01); *A61B 6/0407* (2013.01)

(58) Field of Classification Search
CPC ... A61B 6/0407; A61B 6/0428; A61B 6/0457; A61B 6/4233; A61B 6/4452; A61B 6/4464; A61B 6/54; A61B 6/542; A61B 6/544

USPC ............................................. 378/62, 95, 165
See application file for complete search history.

(56) References Cited

U.S. PATENT DOCUMENTS

| | | | | |
|---|---|---|---|---|
| 4,896,343 A * | 1/1990 | Saunders | ................. | A61B 6/08 356/3.01 |
| 6,934,362 B2 * | 8/2005 | Scheuering | .......... | A61B 5/4869 378/108 |
| 6,942,385 B2 * | 9/2005 | Fadler | ..................... | A61B 6/08 378/205 |
| 7,054,412 B2 * | 5/2006 | Scheuering | ............ | A61B 6/589 378/108 |
| 7,298,823 B2 * | 11/2007 | Bernhardt | ............ | A61B 6/4035 378/97 |
| 7,489,142 B2 * | 2/2009 | Somers | .................. | A61B 6/102 280/735 |

(Continued)

*Primary Examiner* — Allen C. Ho
(74) *Attorney, Agent, or Firm* — Staas & Halsey LLP

(57) ABSTRACT

An X-ray imaging apparatus comprises an X-ray source for irradiating X-rays to a subject; a sensor mounted on the source; and a controller for obtaining a volume of the subject based on an output value of the sensor, determining a degree of obesity of the subject based on the volume, and controlling an irradiation level of the X-rays based on the degree of obesity of the subject, wherein the output value of the sensor comprises, if the sensor comprises multiple image sensors, tilting angles of the multiple image sensors while the X-ray source is being shifted. An X-ray imaging apparatus and method for controlling the same where characteristics, e.g., a degree of obesity, of a subject may be automatically detected. Based on the detected characteristics of the subject, an intensity of X-rays may be automatically controlled, thereby improving the quality of the X-ray image.

25 Claims, 26 Drawing Sheets

(56) References Cited

U.S. PATENT DOCUMENTS

| | | | | |
|---|---|---|---|---|
| 7,660,390 B2* | 2/2010 | Bernhardt | ............... | A61B 6/504 |
| | | | | 378/116 |
| 7,682,079 B2* | 3/2010 | Schwartz | ............. | A61B 5/0555 |
| | | | | 378/117 |
| 7,801,276 B2* | 9/2010 | Ohta | ..................... | G01T 1/2012 |
| | | | | 378/115 |
| 8,433,038 B2* | 4/2013 | Zeng | ........................ | A61B 6/00 |
| | | | | 378/205 |
| 8,675,814 B2* | 3/2014 | Akahori | ................ | A61B 6/032 |
| | | | | 378/196 |
| 8,755,490 B2* | 6/2014 | Takamura | ................ | A61B 6/00 |
| | | | | 378/108 |
| 8,931,124 B2* | 1/2015 | Daley | .................... | A61G 13/04 |
| | | | | 5/600 |
| 9,462,985 B2* | 10/2016 | Hu | ........................ | A61B 6/547 |

* cited by examiner

FIG. 12
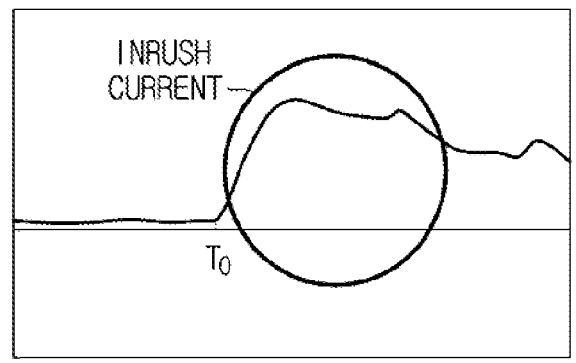
(a)
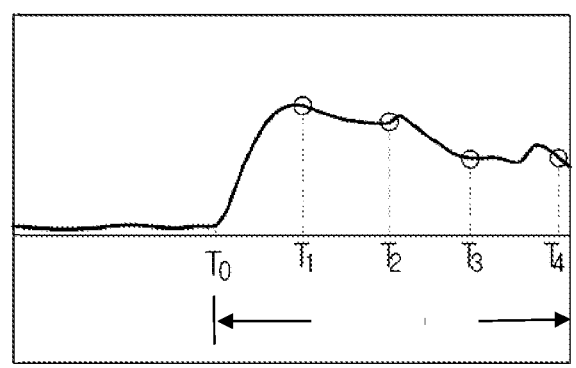
(b)
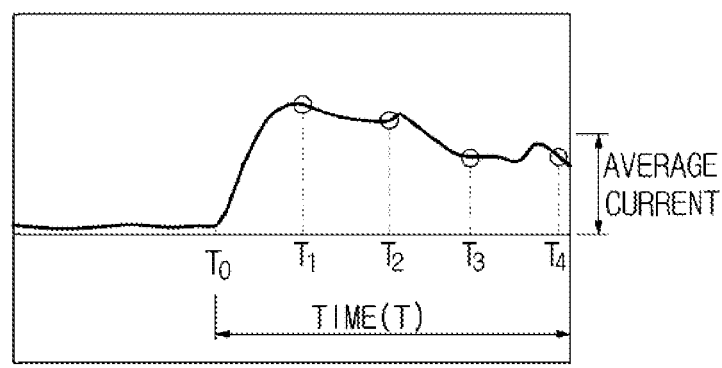
(c)

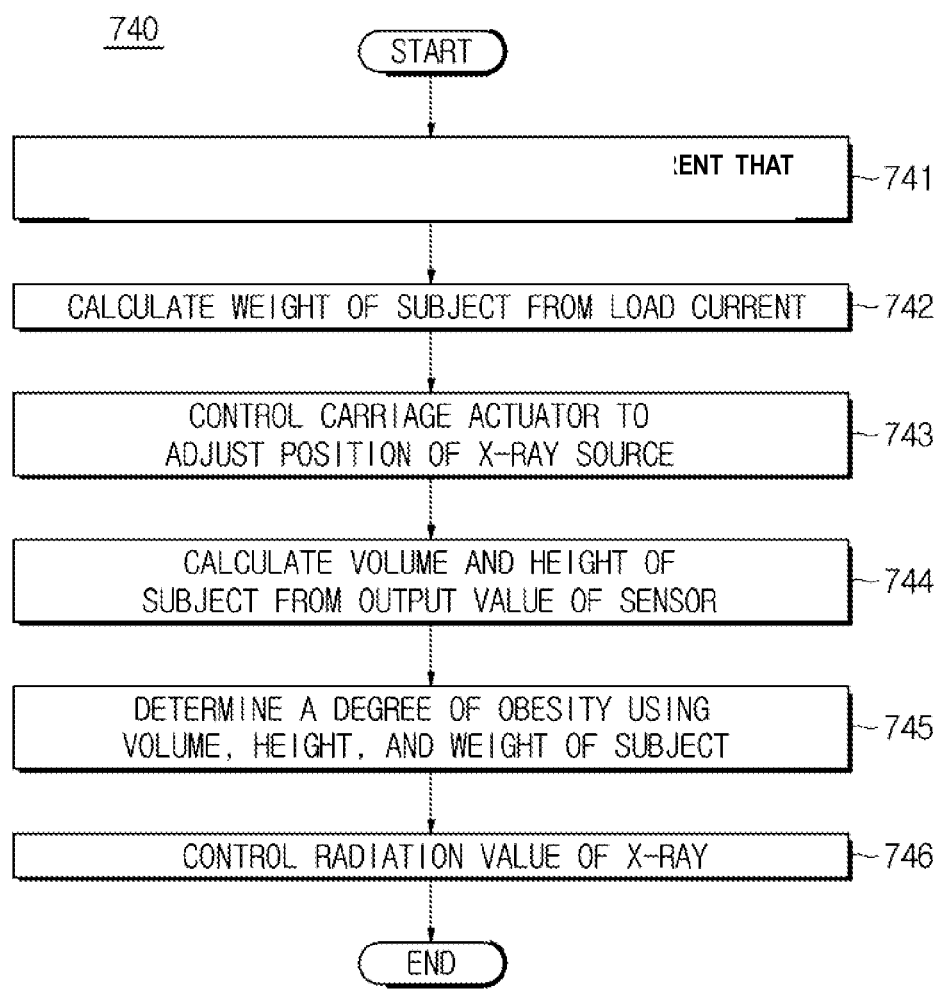

X-RAY IMAGING APPARATUS AND METHOD FOR CREATING X-RAY IMAGE

CROSS-REFERENCE TO RELATED APPLICATION(S)

This application claims the benefit under 35 U.S.C. §119 (a) of Korean patent applications filed on Jul. 21, 2014 and Apr. 29, 2015 in the Korean Intellectual Property Office and assigned Serial Nos. 10-2014-0091732 and 10-2015-0060383, respectively, the entire disclosure of which is incorporated hereby incorporated by reference.

BACKGROUND

1. Field

One or more embodiments of the present disclosure relate to an X-ray imaging apparatus and method for controlling the same, which detects characteristics of a subject.

2. Description of the Related Art

X-ray imaging apparatuses are devices that use X-radiation to obtain images of the inside of subjects. The X-ray imaging apparatus images the inside of a subject in a non-invasive method by irradiating X-rays to the subject and detecting X-rays that have penetrated the subject. Accordingly, a medical X-ray imaging apparatus may be used to diagnose injuries or diseases of the inside of a subject, which may be otherwise difficult to see.

The X-ray imaging apparatus includes an X-ray source for generating and irradiating X-rays to a subject and an X-ray detector for detecting X-rays that have penetrated the subject. With a recent trend toward automation, interest in automation of the X-ray imaging apparatus including the X-ray source and X-ray detector is also growing.

For example, a need exists for development of automation of the X-ray imaging apparatus, such as automatically detecting the position of the X-ray detector and performing auto tracking or auto centering, automatically detecting characteristics of the subject, automatically moving the position of the X-ray source or X-ray detector according to the detected characteristics of the subject, automatically controlling the intensity of the X-rays according to the detected characteristics of the subject, and so on.

SUMMARY

The present disclosure provides an X-ray imaging apparatus and method for controlling the same, which automatically detects characteristics of a subject.

In accordance with an aspect of the present disclosure, an X-ray imaging apparatus is provided. The X-ray imaging apparatus includes an X-ray source for irradiating X-rays to a subject; a sensor mounted on the X-ray source; and a controller for obtaining a volume of the subject based on an output value of the sensor, determining a degree of obesity of the subject based on the volume, and controlling an irradiation level of the X-rays based on the degree of obesity of the subject, wherein the output value of the sensor comprises, if the sensor comprises multiple image sensors, tilting angles of the multiple image sensors while the X-ray source is being shifted.

The sensor may further include a proximity sensor.

The output value of the sensor may include pixel values of an image captured by the multiple image sensors.

The controller may be configured to detect an outline of the subject from the image based on a change in the pixel value and obtain a volume and height of the subject based on the outline.

The X-ray imaging apparatus may further include a source actuator for shifting the X-ray source.

The controller may be configured to control the source actuator to shift the X-ray source in the direction of the length of a scanning table, if the sensor includes a proximity sensor or multiple image sensors.

The output value of the sensor may include an output voltage output from the proximity sensor while the X-ray source is being shifted.

The controller may be configured to convert the output voltage to a distance to the proximity sensor, and obtain a volume of the subject based on the converted distance.

The controller may be configured to obtain a first distance by converting a highest output voltage among the output voltages, obtain a second distance by converting a lowest output voltage among the output voltages, and obtain a volume of the subject from a difference between the first distance and the second distance.

The controller may be configured to obtain a height of the subject from a difference between a shifted distance of the X-ray source and a part of the shifted distance in which the proximity sensor outputs the lowest output voltage.

The multiple image sensors may have the same focal point.

The controller may be configured to calculate a distance from the multiple image sensors using the following equation:

$$d = \frac{d'}{\tan(90° - \theta_1) + \tan(90° - \theta_2)}$$

where d' indicates a distance between the multiple image sensors, θ1 and θ2 indicate tilting angles of the multiple image sensors for a focal point, and d indicates a distance to the focal point from the multiple image sensors.

The controller may be configured to obtain a volume of the subject from a difference between a maximum distance and a minimum distance among the calculated distances.

The controller may be configured to obtain a height of the subject from a difference between a shifted distance of the X-ray source and a part of the shifted distance in which the minimum distance is calculated.

The irradiation level of the X-rays may correspond to an intensity or amount of irradiation of the X-rays.

In accordance with another aspect of the present disclosure, an X-ray imaging apparatus is provided. The X-ray imaging apparatus includes an X-ray source for irradiating X-rays to a subject; a table actuator for shifting a scanning table; and a controller for determining a weight of the subject based on an output value of the table actuator and controlling an irradiation level of the X-rays based on the weight of the subject.

The table actuator may include at least one of a current sensor, a magnetic sensor, and a current sensing circuit.

The output value of the table actuator may include a load current that flows in the table actuator while the scanning table is being shifted in the up/down direction.

The controller may be configured to extract measured currents from the load current flowing in the table actuator at a sample rate, and calculate an average current from the extracted measured currents using the following equation:

$$X_{rms} = \sqrt{\frac{1}{n}(X_1^2 + X_2^2 + \ldots + X_n^2)}$$

where Xi (i=1, 2, . . . , n) refers to extracted measured currents, n refers to the number of extraction times, and Xrms refers to an average current.

The controller may be configured to determine a degree of obesity of the subject by comparing the load current with at least one predetermined threshold current.

The controller may be configured to determine a weight of the subject based on the load current, and determine a degree of obesity of the subject by comparing the determined weight of the subject and at least one weight threshold.

In accordance with another aspect of the present disclosure, an X-ray imaging apparatus is provided. The X-ray imaging apparatus includes an X-ray source for irradiating X-rays to a subject; a sensor mounted on the X-ray source; a table actuator for shifting a scanning table; and a controller for obtaining a height of the subject based on an output value of the sensor, obtaining a weight of the subject based on an output value of the table actuator, and controlling an irradiation level of the X-rays based on the height and weight of the subject.

In accordance with another aspect of the present disclosure, a method for controlling an X-ray imaging apparatus is provided. The method includes obtaining a volume of a subject based on an output value of a sensor mounted on an X-ray source; determining a degree of obesity of the subject based on the volume of the subject; and controlling an irradiation level of X-rays to be irradiated by the X-ray source, based on the degree of obesity of the subject, wherein the output value of the sensor comprises, if the sensor comprises multiple image sensors, tilting angles of the multiple image sensors while the X-ray source is being shifted.

In accordance with another aspect of the present disclosure, a method for controlling an X-ray imaging apparatus is provided. The method includes shifting a scanning table in the up/down direction; determining a weight of the subject based on an output value of a table actuator while the scanning table is shifted; and controlling an irradiation level of X-rays to be irradiated by the X-ray source, based on the weight of the subject.

In accordance with another aspect of the present disclosure, a method for controlling an X-ray imaging apparatus is provided. The method includes obtaining a height of a subject based on an output value of a sensor mounted on an X-ray source; obtaining a weight of the subject based on an output value of a table actuator that shifts a scanning table; and controlling an irradiation level of X-rays to be irradiated by the X-ray source, based on the height and weight of the subject.

In accordance with another aspect of the present disclosure, a method for controlling an X-ray source of an X-ray imaging apparatus is provided. The method includes determining a degree of obesity of a subject and controlling, using a hardware-based processor, an intensity of X-rays to be radiated by the X-ray source based on the determined degree of obesity of the subject.

In accordance with another aspect of the present disclosure, a method for controlling an X-ray imaging apparatus is provided. The method includes determining a height, weight and volume of an X-ray object, and controlling an X-radiation level of an X-ray irradiation of the object based on the height, weight and volume. The height may be determined by an outline of a captured image of the object. The volume may be determined by the height and a thickness of the object relative to a reference. The thickness of the object may be relative to a reference. The weight may be determined by a force needed to move a carrier on which the object is positioned. The weight may be determined by a table motor load current when the table is moved vertically and horizontally.

Other aspects, advantages, and salient features of the disclosure will become apparent to those skilled in the art from the following detailed description, which, taken in conjunction with the annexed drawings, discloses exemplary embodiments of the disclosure

BRIEF DESCRIPTION OF THE DRAWINGS

The above and other features and advantages of the present disclosure will become more apparent by describing in detail exemplary embodiments thereof with reference to the attached drawings in which:

FIG. 12 shows plots for explaining how to calculate an average current;

FIG. 26 is a flowchart illustrating a method for controlling an X-ray imaging apparatus, according to still another embodiment of the present disclosure.

Throughout the drawings, like reference numerals will be understood to refer to like parts, components, and structures.

DETAILED DESCRIPTION

Figure 1:
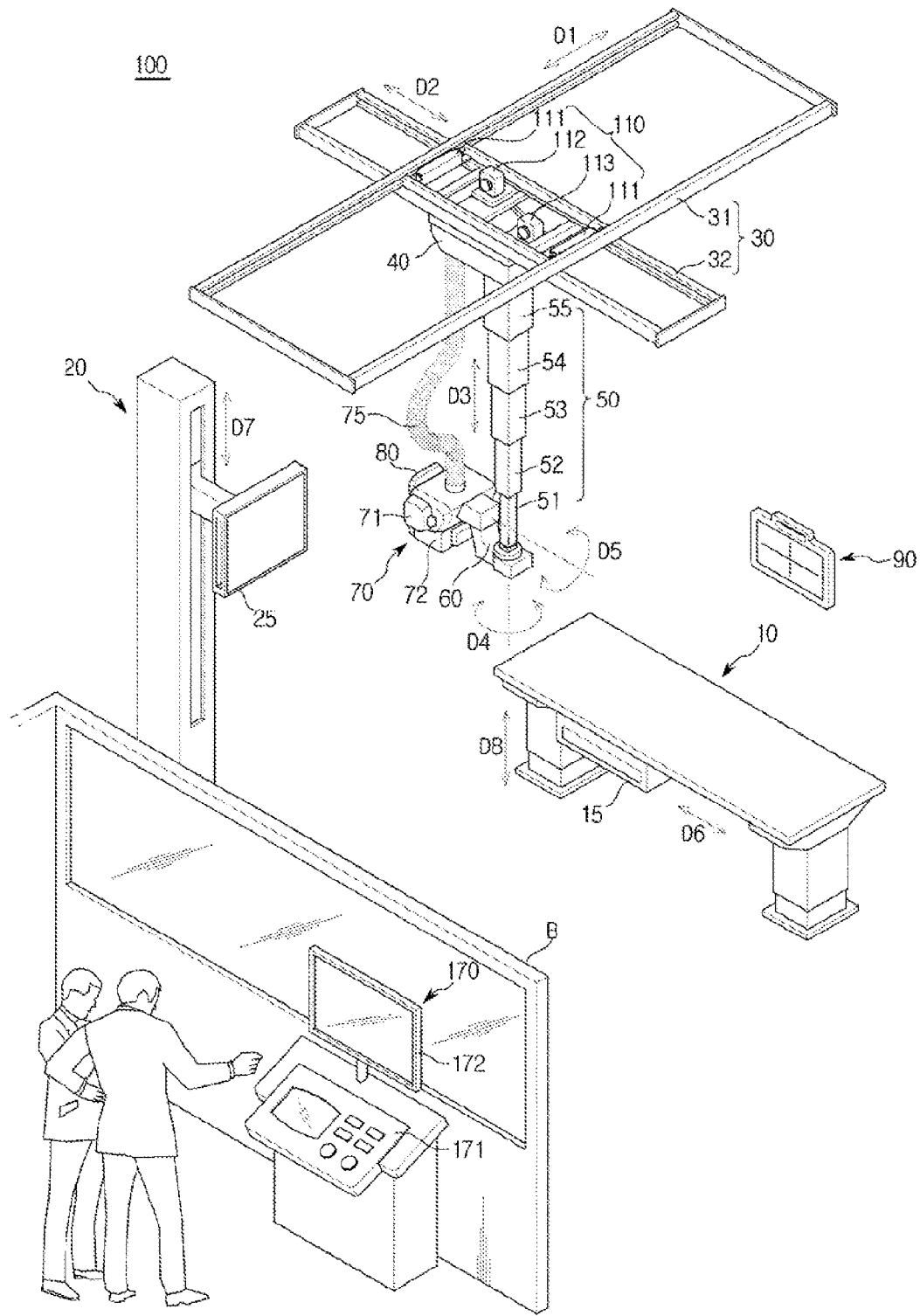
FIG. 1 is a perspective view illustrating an X-ray imaging apparatus.

The present disclosure will now be described more fully with reference to the accompanying drawings, in which exemplary embodiments of the disclosure are shown. The disclosure may, however, be embodied in many different forms and should not be construed as being limited to the embodiments set forth herein; rather, these embodiments are provided so that this disclosure will be thorough and complete, and will fully convey the concept of the disclosure to those skilled in the art. Like reference numerals in the drawings denote like elements, and thus their description will be omitted. In the description of the present disclosure, if it is determined that a detailed description of commonly-used technologies or structures related to the embodiments of the present disclosure may unnecessarily obscure the subject matter, the detailed description will be omitted. It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section.

Embodiments and features as described and illustrated in the present disclosure are only examples, and various modifications thereof may also fall within the scope of the disclosure.

Embodiments of an X-ray imaging apparatus and method for controlling the same will now be described in detail with reference to accompanying drawings. Like reference numerals indicate like elements throughout the specification.

Figure 2:
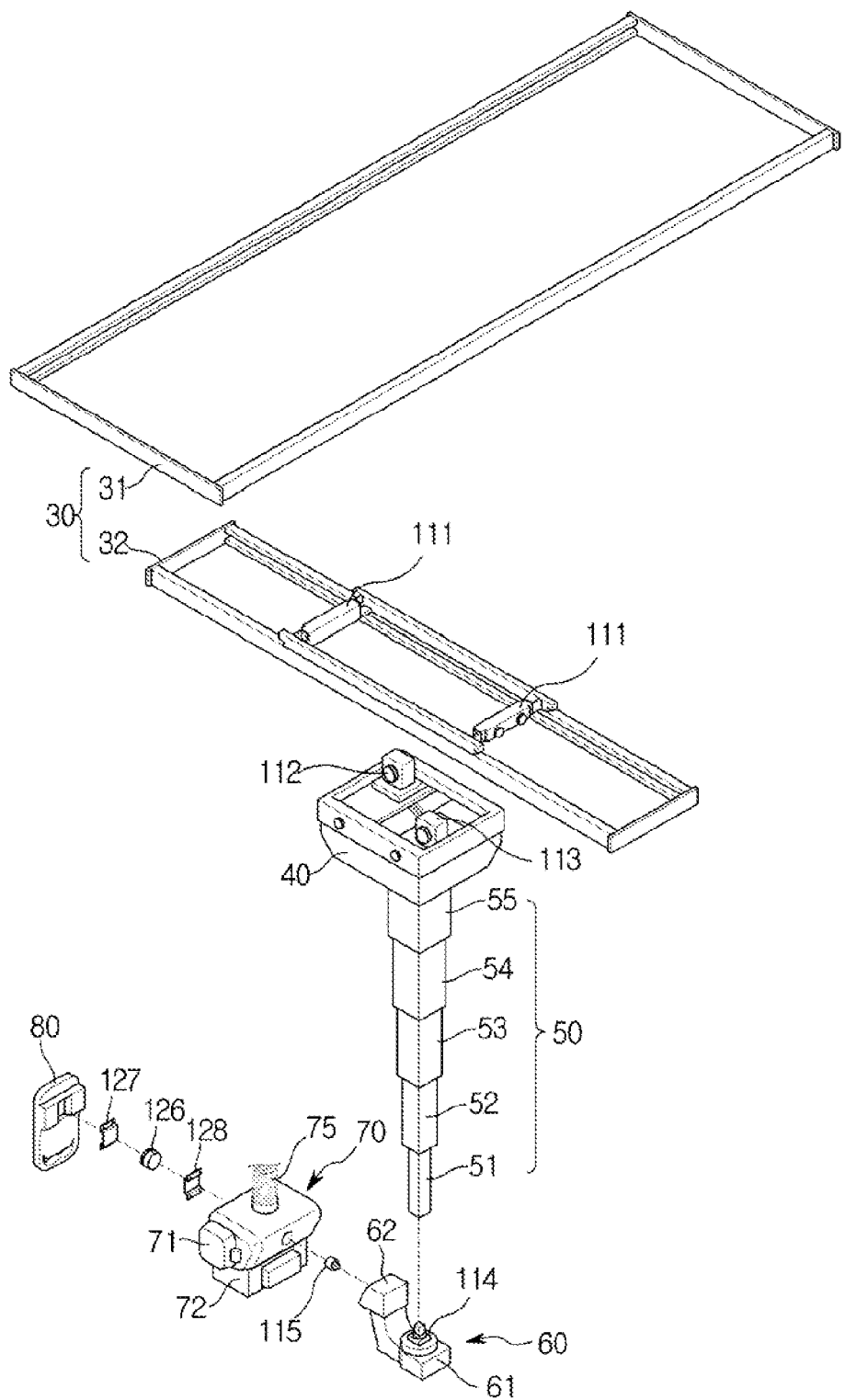
FIG. 2 is an exploded view of an X-ray imaging apparatus.

FIG. 1 is a perspective view illustrating an X-ray imaging apparatus, and FIG. 2 is an exploded view of an X-ray imaging apparatus.

Referring to FIGS. 1 and 2, an X-ray imaging apparatus 100 may include guide rail 30, moving carriage 40, post frame 50, actuator 110, 114, and 115, X-ray source 70, X-ray detector 100, operation unit 80, and workstation 170. The X-ray imaging apparatus 100 may further include scanning table 10 on which the X-ray detector 90 may be mounted, and scanning stand 20.

The guide rail 30, moving carriage 40, post frame 50, and the like may serve to move the X-ray source 70 toward a subject, such as a human subject situated on scanning table 10.

The guide rail 30 may include a first guide rail 31 and a second guide rail 32 installed to form a predetermined angle between them. The first and second guide rails 31 and 32 may be installed to form right angles with each other.

The first guide rail 31 may be installed on the ceiling of an examination room where the X-ray imaging apparatus is placed. The second guide rail 32 may be located below the first guide rail 31 and engaged with the first guide rail 31 to be moved slidingly with respect to the first guide rail 31. The first guide rail 31 may have a roller (not shown), for example, that moves along the first guide rail 31. The second guide rail 32 may be connected to the roller and moved along the first guide rail 31.

A first direction D1 is defined as a direction in which the first guide rail 31 extends, and a second direction D2 is defined as a direction in which the second guide rail 32 extends. The first and second directions D1 and D2 are perpendicular to each other and parallel to the ceiling of the examination room.

The moving carriage 40 is located below the second guide rail 32 such that it may be moved along the second guide rail 32. The moving carriage 40 may have a roller (not shown) for example, arranged to move along the second guide rail 32. Accordingly, the moving carriage 40 is able to move with the second guide rail 32 in the first direction D1 and move along the second guide rail 32 in the second direction D2. The post frame 50 is fixed to and located below the moving carriage 40. The post frame 50 may include multiple posts 51, 52, 53, 54, and 55.

The multiple posts 51, 52, 53, 54, and 55 may be foldably linked with each other, and thus the length of the post frame 50 may increase or decrease in an up or down direction in the examination room while being fixed to the moving carriage 40. In an alternative embodiment, the multiple posts 51, 52, 53, 54, and 55 may be nested or inserted one within another to allow a telescoping movement to increase or decrease the length of the post frame in an up or down direction.

A third direction D3 is defined as the direction in which the length of the post frame 50 increases or decreases. Thus, the third direction D3 is perpendicular to the first and second directions D1 and D2.

The X-ray source 70 is a device for irradiating X-rays to or toward a subject.

The subject (or object) as herein used may be, but is not exclusively, a living body of a human or animal, and any object whose internal structure may be imaged by the X-ray imaging apparatus 100. However, for convenience of explanation, it is assumed herein that the subject is a human.

The X-ray source 70 may include an X-ray tube 71 for generating X-rays and a collimator 72 for guiding the X-rays toward the subject, which will be described later in more detail.

A rotating joint 60 may be arranged between the X-ray source 70 and the post frame 50.

The rotating joint 60 combines the X-ray source 70 with the post frame 50 and supports the weight applied to the X-ray source 70. The rotating joint 60 may include a first rotating joint 61 combined with the lower post 51 of the post frame 50 and a second rotating joint 62 combined with the X-ray source 70.

The first rotating joint 61 is arranged to be able to rotate around the central axis of the post frame 50 that extends in the up/down direction in the examination room. Accordingly, the first rotating joint 61 may rotate on the plane perpendicular to the third direction D3. The rotation direction of the first rotating joint 61 may be newly defined as a fourth direction D4 corresponding to a rotation direction of the axis parallel to the third direction D3.

The second rotating joint 62 is arranged to be able to rotate on the plane perpendicular to the ceiling of the examination room. Accordingly, the second rotating joint 62 may rotate in the rotation direction of the axis parallel to the first direction D1 or the second direction D2. The rotation direction of the second rotating joint 62 may be newly defined as a fifth direction D5 corresponding to the rotation direction of the axis that extends in the first or second direction D1 or D2. The X-ray source 70 may be coupled with the rotating joint 60 and rotationally moved in the fourth or fifth direction D4 or D5. In addition, the X-ray source 70 may be coupled with the post frame 50 by the rotating joint 60 and shifted straight in the first, second, or third direction D1, D2, or D3.

To shift the X-ray source 70 in any of the first to fifth directions D1 to D5, there may be corresponding actuators 110, 114, and 115. The actuators 110, 114, and 115 may include motors and motor drivers to drive the motors, and the motors may be electric motors driven electrically.

The actuator 110 may include actuators 111, 112, and 113 that correspond to the first to third directions D1, D2, and D3, and the actuators 114 and 115 may correspond to the fourth and fifth directions D4 and D5.

The actuators 111, 112, 113, 114, and 115 may be arranged in various positions by considering design convenience. For example, the first actuator 111 that shifts the second guide rail 32 in the first direction D1 may be arranged around the first guide rail 31; the second actuator 112 that shifts the moving carriage 40 in the second direction D2 may be arranged around the second guide rail 32; and the third actuator 113 that increases or decreases the length of the post frame 50 in the third direction D3 may be arranged inside of the moving carriage 40. Furthermore, the fourth actuator 114 that rotationally moves the X-ray source 70 in the fourth direction D4 may be arranged around the first rotating joint 61, and the fifth actuator 115 that rotationally moves the X-ray source 70 in the fifth direction D5 may be arranged around the second rotating joint 62.

Here, the first, second, and third actuators 111, 112, and 113 that shift the moving carriage 40 are collectively defined as a carriage actuator 110.

Each of the actuators 111, 112, 113, 114, and 115 may be coupled with a power delivery means (not shown) to move the X-ray source 70 straight or rotationally in any of the first to fifth directions D1 to D5. The power delivery means (not shown) may be a commonly-used belt and pulley, chain and sprocket, shaft, etc.

A side of the X-ray source 70 has the operation unit 80 arranged to provide a user interface. The 'user' as used herein may be a medical person who performs diagnosis on the subject with the X-ray imaging apparatus 100, including a doctor, a radiographer, a nurse, etc., but is not limited thereto and may be anyone who uses the X-ray imaging apparatus 100.

Figure 3:
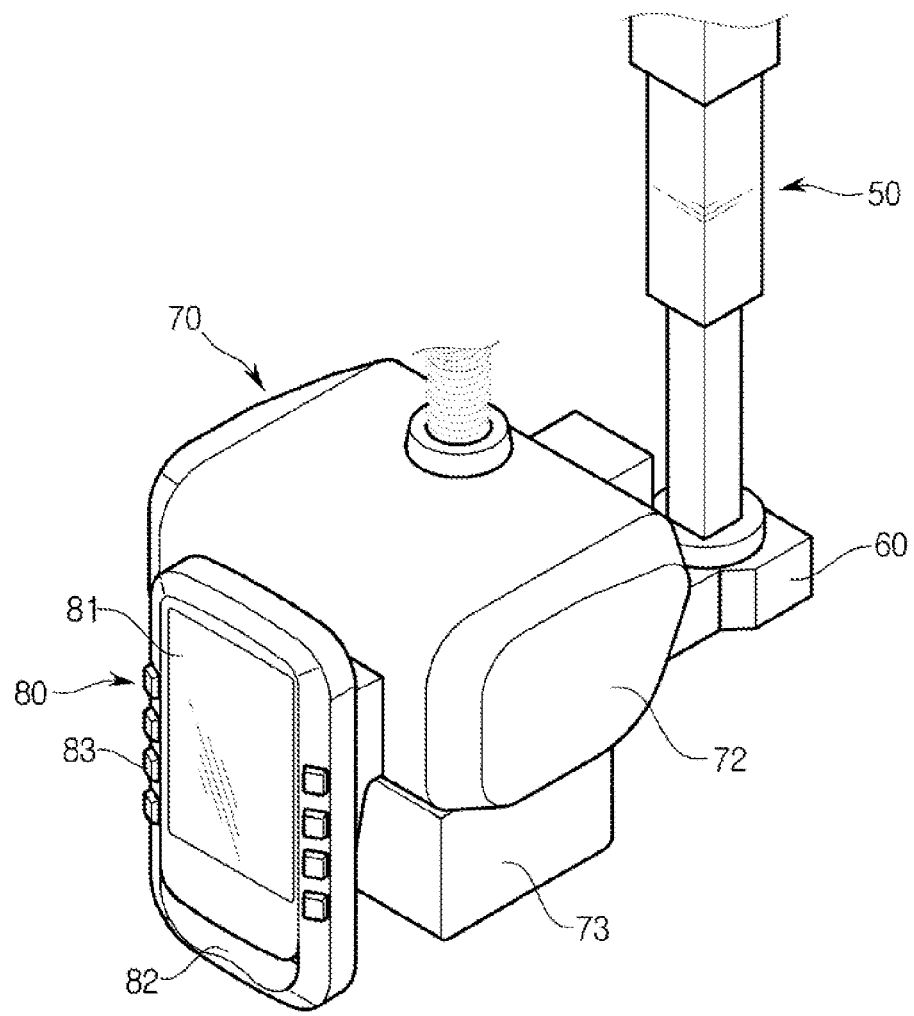
FIG. 3 is a perspective view illustrating an operation unit of an X-ray imaging apparatus.

FIG. 3 is a perspective view illustrating an operation unit of an X-ray imaging apparatus.

Referring to FIG. 3, the operation unit 80 may include buttons 83 and a display panel 81. The user may press any of the buttons 83 or may touch the display panel 81 to enter information or to operate different devices. The display panel 81 may include, but not exclusively, a Cathode Ray Tube (CRT), a Digital Light Processing (DLP) panel, a Plasma Display Panel (PDP), a Liquid Crystal Display (LCD) panel, an Electro Luminescence (EL) panel, an Electrophoretic Display (EPD) panel, an Electrochromic Display (ECD) panel, a Light Emitting Diode (LED) panel, an Organic LED (OLED) panel, or the like.

The operation unit 80 may include a handle 82 for a user to grip it. Specifically, the user may grip the handle 82 or apply some force or torque to the handle 82 to shift the X-ray source 70 straight to the first direction D1 or the third direction D3 or to rotationally shift the X-ray source 70 to the fourth direction D4 or the fifth direction D5. Although FIG. 3 shows the handle 82 arranged below the operation unit 80, the position of the handle 80 may be arranged anywhere in the operation unit 80.

The operation unit 80 may include a Central Processing Unit (CPU) implemented with e.g., a microprocessor, a Graphic Processing Unit (GPU), and various types of storage devices, which may all be arranged on a built-in Printed Circuit Board (PCB). The operation unit 80 may also be referred to as a "Tube Head Board" or "THB" because the operation unit 80 includes the PCB and is arranged on a side of the X-ray source 70.

Turning back to FIG. 1, the workstation 170 may include input unit 171 and display unit 172, providing a user interface that may operate in cooperation with the operation unit 80. Accordingly, the user may enter information with respect to X-ray scanning, or may operate individual devices. For example, the user may set up a scanning condition for a part to be scanned with the workstation 170, or enter a command to shift the moving carriage 40 or X-ray source 70 or a command to start X-ray scanning. In addition, the user may view images obtained in the process of the X-ray scanning with the workstation 170.

The input unit 171 may include many different buttons, a keyboard, mouse, track ball, various levers, handle, stick, or any other hardware input devices for the user input. The input unit 171 may be arranged on the top of the workstation 170 as shown in FIG. 1, or may be contained in a lower part of the workstation 170 if it is implemented with a foot switch or foot pedal.

The input unit 171 may also include a Graphical User interface (GUI) on a software input device, such as a touch pad for the user input.

The touch pad may be implemented with a Touch Screen Panel (TSP), thus forming an interlayer structure with the second display unit 172, which will be described later.

Similar to the display panel 81 of the operation unit 80, the display unit 172 may include, but not exclusively, a Cathode Ray Tube (CRT), a Digital Light Processing (DLP) panel, a Plasma Display Panel (PDP), a Liquid Crystal Display (LCD) panel, an Electro Luminescence (EL) panel, an Electrophoretic Display (EPD) panel, an Electrochromic Display (ECD) panel, a Light Emitting Diode (LED) panel, an Organic Light Emitting Diode (OLED) panel, or the like.

As noted above, the display unit 172 may also be used as an input device in addition to the display functionality if implemented with the TSP to form with the interlayer structure the touch pad.

Furthermore, the workstation 170 may have a built-in PCB including various processing units, such as CPU or GPU, or both, and various storage devices. Accordingly, the workstation 170 may contain the main components of the X-ray imaging apparatus 100, including a controller (for example, a controller 500 of FIG. 4) to make various decisions for operating the X-ray imaging apparatus 100 or generate various control signals.

A blocking wall B is located between the workstation 170 and the examination room to block the X-rays, so that the user may enter information or operate devices without being exposed to the X-rays during the X-ray scanning.

The X-ray detector 90 is a device for detecting X-rays that have penetrated the subject.

The X-ray detector 90 may be mounted on the scanning table 10 or scanning stand 20 during the X-ray scanning. The scanning table 10 has a table tray 15 for housing the X-ray detector 90, which may be shifted in the direction of the length of the scanning table 10. Likewise, the scanning stand 20 has a stand holder 25 for holding the X-ray detector 90, which may be shifted in the direction along the length of the scanning stand 20. In this regard, the direction of the length of the scanning table 10 and the direction of the length of the scanning stand 20 may be defined as sixth and seventh directions D6 and D7, respectively. The table tray 15 containing the X-ray detector 90, or the stand holder 25 may scan the whole part or a particular part of the subject while being shifted in the sixth D6 or seventh direction D7.

The scanning table 10 (or subject carrier) may include a support 12 that supports the scanning table 10 and adjusts the height of the scanning table 10, and the support 12 may have a table actuator (see 200 of FIG. 4) arranged to shift the support 12 in the up/down direction. The up/down direction of the support 12 may be defined as the eighth direction D8, and the table actuator will be described in more detail later.

The appearance of an X-ray imaging apparatus has thus far been described, and features and the functionality of the features of the X-ray imaging apparatus 100 for diagnosing degree of obesity will now be described in more detail.

Figure 4:
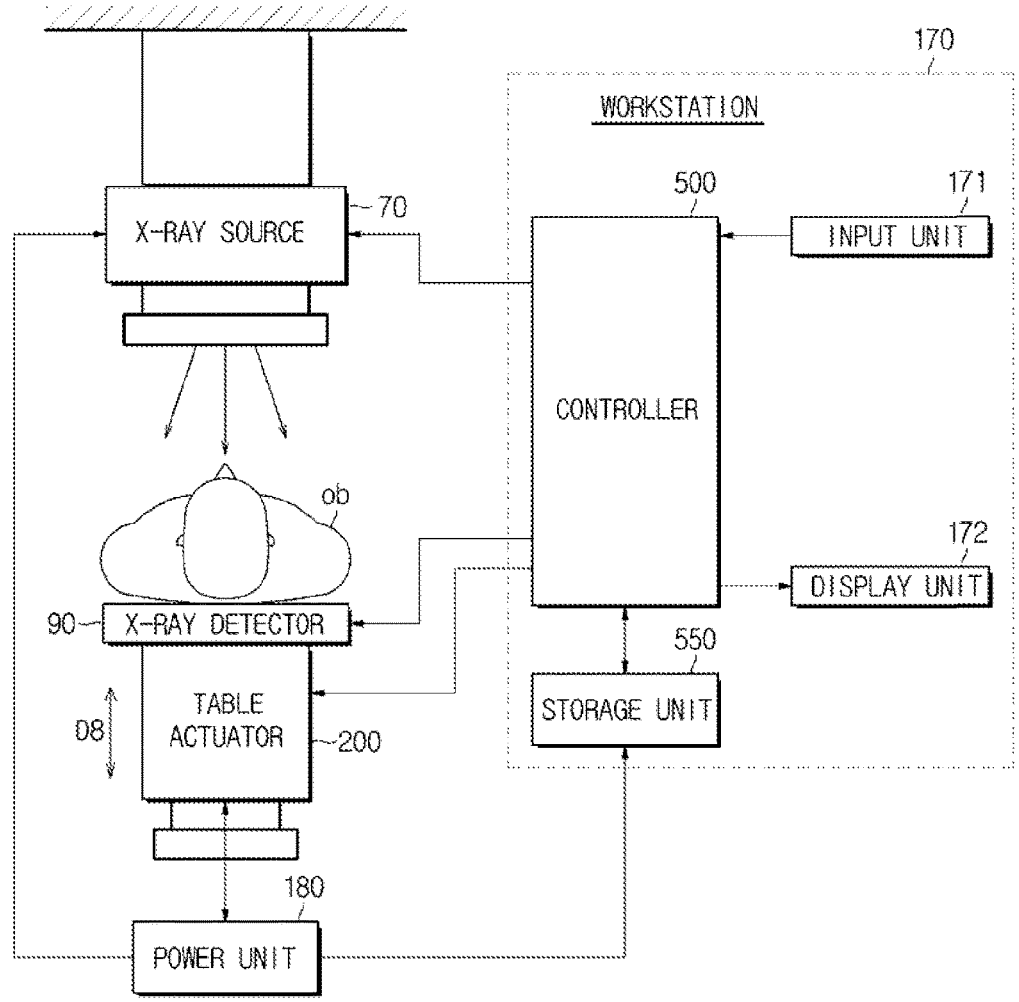
FIG. 4 is a control block diagram of an X-ray imaging apparatus, according to an embodiment of the present disclosure.

FIG. 4 is a control block diagram of an X-ray imaging apparatus, according to an embodiment of the present disclosure.

Referring to FIG. 4, an X-ray imaging apparatus 101 may include, for example, power unit 180, X-ray source 70, X-ray detector 90, table actuator 200, controller 500, storage unit 550, input unit 171, and display unit 172.

The power unit 180 receives external power or internal power and supplies the power to all the components of the X-ray imaging apparatus 101, such as the X-ray source 70, the X-ray detector 90, etc. The power unit 180 supplies the power required for operations of the components in the form of a current, which may be a direct current (DC) or an alternating current (AC).

Figure 5:
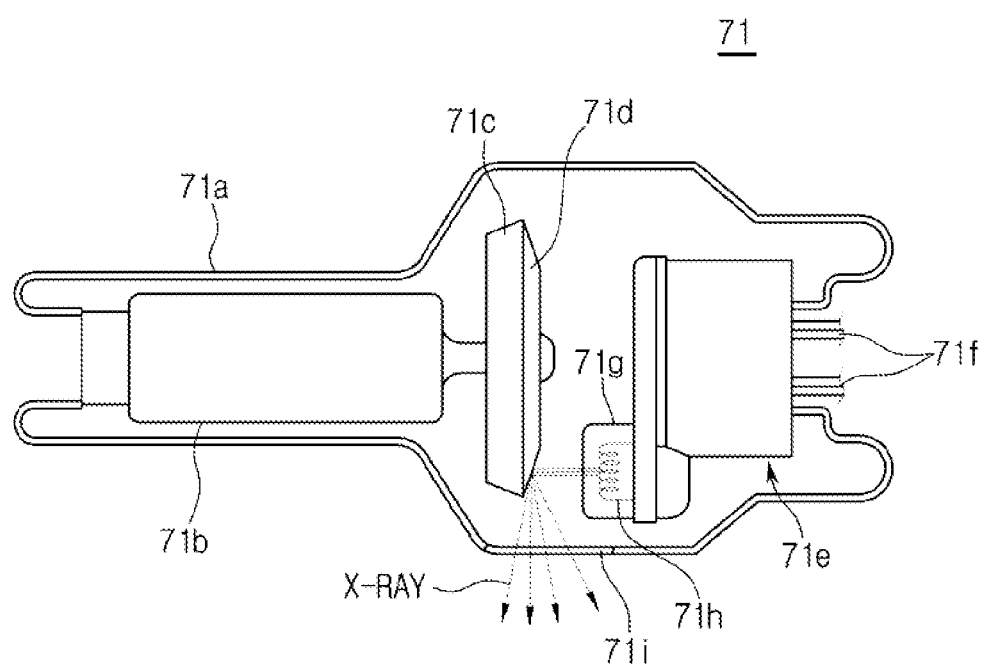
FIG. 5 is a cross-sectional view illustrating an internal structure of an X-ray tube.

The X-ray source 70 may generate X-rays and may irradiate them to a subject, and include X-ray tube 71 for generating X-rays, as shown in FIG. 5. FIG. 5 is a cross-sectional view illustrating an internal structure of the X-ray tube 71.

The X-ray tube 71 may be implemented as a bipolar vacuum tube that includes positive and negative electrodes 71c and 71e, and the body of the vacuum tube may be a glass tube 71a made of e.g., hardened silicon glass.

The negative electrode 71e may include a filament 71h and a focusing electrode 71g that focuses electrons, the focusing electrode 71g being also called a focusing cup. Thermions (electrically charged particles or ions) are generated by making the inside of the glass tube 71a in a high vacuum state of about 10 mmHg and heating the filament 71h of the negative electrode 71e to a high temperature. As an example of the filament 71h, a tungsten filament may be used, which may be heated by applying a current to an electric wire 71f coupled with the filament 71h. However, the embodiment is not limited to the occasion where the negative electrode 71e employs the filament 71h, and it is also possible to have a carbon nano-tube for the negative electrode 71e, which may be driven by high-rate pulses.

The positive electrode 71c is mainly formed of copper, and a target material 71d is applied or disposed on the side that faces the negative electrode 71e. The target material may include a high resistive material, such as Cr, Fe, Co, Ni, W, Mo, or the like. The higher the melting point of the target material, the smaller the focal spot size.

When a high voltage is applied across the negative and positive electrodes 71e and 71c, thermions get accelerated and collide with the target material 71d of the positive electrode, thus generating an X-ray. The X-ray is radiated out through the window 71i that may use a thin film of Beryllium.

The target material 71d may be rotated by a rotor 71b. While the target material 71d is rotating, heat build-up rate may increase more than ten times per unit area as compared with an occasion where the target material 71d is stationary, and the focal spot size may decrease.

A voltage applied across the negative and positive electrodes 71e and 71c of the X-ray tube 71 is called a tube voltage whose magnitude may be represented by a crest value kVp (kilo voltage peak). As the tube voltage increases, the speed of the thermions increases and as a result, energy of X-radiation (energy of photon radiation) produced from collision of the thermion with the target material increases. Current flowing through the X-ray tube 71 is called tube current, which may be represented by an average value mA. As the tube current increases, the amount of X-rays (the number of photons) increases. That is, the energy of X-radiation may be controlled by the tube voltage and the amount of X-rays may be controlled by the tube current.

The X-ray detector 90 is a device for detecting X-rays radiated from the X-ray source 70 that have penetrated the subject. This X-ray detection may be performed by a detection panel 120 inside the X-ray detector 90. Furthermore, the detection panel 120 converts the detected X-ray to an electric signal, to obtain an X-ray image of the inside of the subject.

The detection panel 120 may be classified based on a material composition method, a method for converting the detected X-ray to an electric signal and a method for obtaining an electric signal.

First, the detection panel 120 may be divided into a case where it is formed of a single element and a case where it is formed of composite elements, based on the material composition method.

When the detection panel 120 is formed of a single material, a section that detects the X-ray and generates an electric signal and a section that reads and processes the electric signal may be formed of a semiconductor of a single material or may be manufactured with a single process, for example, using a Charge Coupled Device (CCD) or a Complementary Metal Oxide Semiconductor (CMOS).

When the detection panel 120 is formed of composite elements, a section that detects the X-ray and generates an electric signal and a section that reads and processes the electric signal may be formed of different materials or manufactured with different processes. For example, there may be an occasion where photo detectors, such as, photo diodes, CCD, CdZnTe, etc., are used to detect an X-ray and CMOS Read Out Integrated Circuits (ROICs) are used to read and process the electric signal; an occasion where strip detectors are used to detect an X-ray and the CMOS ROICs are used to read and process the electric signal; an occasion in which a-Si or a-Se flat panel systems are used, and so on.

Furthermore, the detection panel 120 may have two types, a first type having direct conversion scheme and a second type having an indirect conversion scheme based on the method for converting the X-ray to an electric signal.

In the direct conversion scheme, when an X-ray radiated, a pair of electron and hole is generated temporarily inside the photo detector and electric potential across both electrodes of the photo detector causes the electron to be moved to the positive electrode and the hole to be moved to the negative electrode. The detection panel 120 converts the movements into an electric signal. In the direct conversion scheme, a material used for the photo detector may be a-Se, CdZnTe, HgI2, PbI2, etc.

In the indirect conversion scheme, the X-ray radiated from the X-ray source 70 reacts with a scintillator to cause photons having a visible wavelength in a visible spectrum to be emitted, and a photo detector detects the photons and converts them to an electric signal. The material used for the photo detector in the indirect conversion scheme may be e.g., a-Si, and the scintillator may be GADOX scintillator in the form of a thin film, or a micro column type or needle structure type CSI (T1).

The detection panel 120 may be divided into a type having a charge integration mode for storing charges for a certain period of time and obtaining a signal from the charges and a type having a photon counting mode for counting the number whenever a signal is generated by a single X-ray photon, based on the method for obtaining the electric signal.

The detection panel 120 may employ any of the aforementioned schemes. The detection panel 120 may also have a two dimensional (2D) array structure that has a plurality of pixels.

Figure 6:
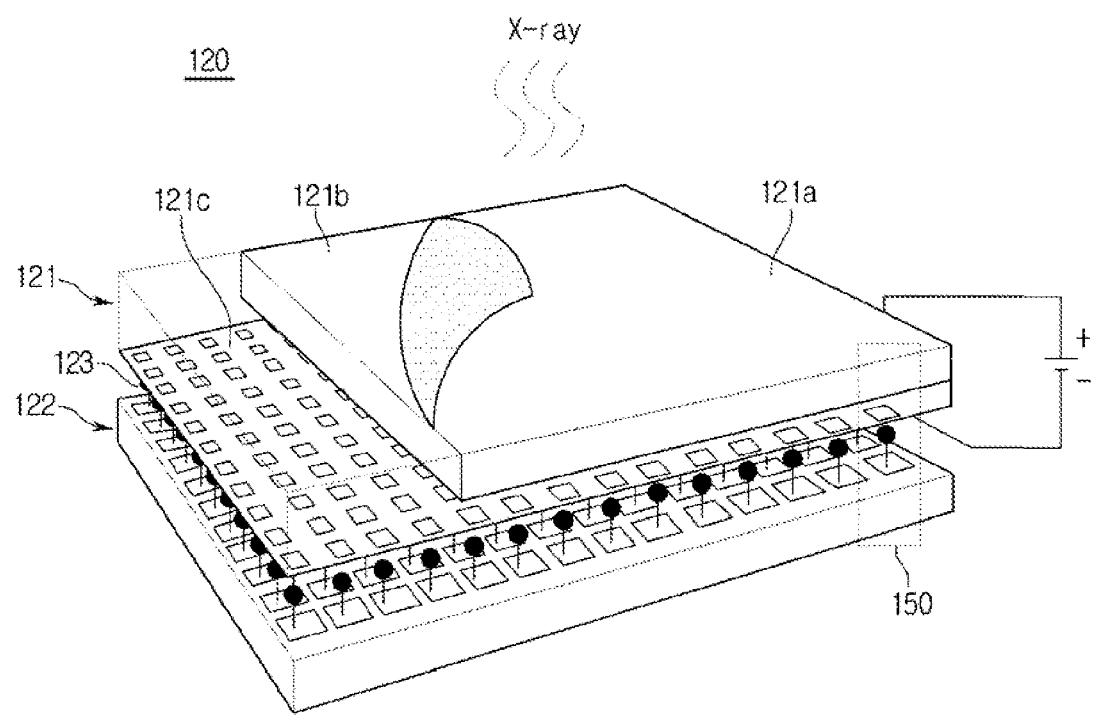
FIG. 6 is a schematic diagram illustrating a structure of a detection panel.

FIG. 6 is a schematic diagram illustrating a structure of a detection panel.

Referring to FIG. 6, the detection panel 120, for example, may include a photo detector device 121 for detecting X-rays and to generate an electric signal and a read-out circuit 122 for reading out the electric signal.

For the photo detector device 121, monocrystal semiconductor materials may be used to secure high resolution, fast response time, and high-dynamic range at low energy and small amount of rays, such as Ge, CdTe, CdZnTe, GaAs, etc.

The photo detector device 121 may be configured in the form of a PIN photo diode in which p-type semiconductor substrate 121c of a 2D array structure is joined with the bottom of the high resistive n-type semiconductor substrate 121b.

The read-out circuit 122 from a CMOS process may have a 2D array structure and may be combined with the p-type substrate 121c of the photo detector device 121 pixel by pixel 150. The combination method may employ a flip chip bonding method that forms, reflows, and presses bumps 123 of PbSn, In, etc.

The X-ray radiated from the X-ray source 70 is attenuated while passing through the subject, due to scattering or absorption, and accordingly the X-ray detector 90 may detect the attenuated X-ray. This attenuation effect of the X-ray occurs differently depending on the constituent material of the subject and the energy level of the radiated X-ray. The extent of attenuation of the X-ray depending on the constituent material of the subject and the energy level of the X-ray is numerically represented by an attenuation coefficient.

Figure 7:
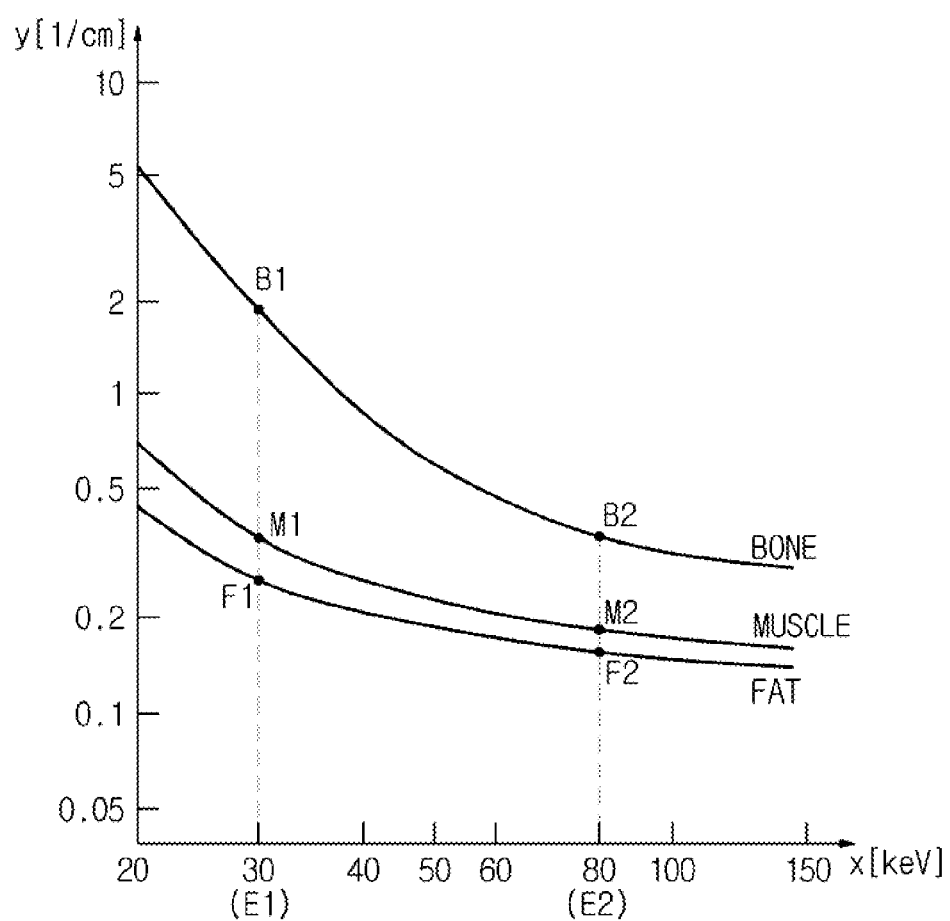
FIG. 7 shows graphs representing relationships between energy and attenuation coefficients per material inside of a subject.

FIG. 7 shows graphs representing relationships between energy and attenuation coefficients for materials inside a subject.

Referring to FIG. 7, the attenuation coefficient changes depending on the constituent material of the inside of the subject. A curve that represents attenuation coefficients of bones is located above a curve that represents attenuation coefficients of soft tissues (e.g., muscle, fat). When an X-ray of energy e.g., E1 is radiated, the attenuation coefficient B1 of bone is greater than that M1 of muscle, which is greater than that F1 of fat. That is, different materials inside the subject have different attenuation coefficients, and the harder the material is, the more the attenuation coefficient increases.

The attenuation coefficient varies depending on the energy level of the radiated X-ray, and a difference in attenuation coefficient between materials also depends on the energy level of the X-ray. It is seen from the graph of FIG. 4 that, when X-rays of energy levels E1 and E2 are irradiated to a subject's bones, an attenuation coefficient B1 at a lower energy level E1 is greater than that B2 at a higher energy level E2. Even in the case that the constituent material of the subject is muscle or fat, it is seen that an attenuation coefficient M1 or F1 at the lower energy level E1 is greater than that M2 or F2 at the higher energy level E2. That is, the lower the energy level of the X-ray irradiated to the subject, the greater the attenuation coefficient.

The attenuation effect of the X-ray may occur differently depending on the thickness of the subject or thickness of a constituent material of the subject, as represented by the following equation 1:

$$I = I_0 \cdot e^{-\mu(E) \cdot T} \quad (1)$$

where I0 refers to an intensity of an X-ray irradiated to a material, I refers to an intensity of an X-ray that has penetrated the material, and μ(E) refers to an attenuation coefficient of the material for the X-ray having an energy level E. T refers to a thickness of the substance through which the X-rays passes.

According to equation 1, even with the same attenuation coefficient, the thicker the material, the greater the extent of the attenuation of the X-ray. In other words, even if X-rays with the same intensity and same energy level are irradiated to the same material, the thicker the material, the less the intensity of the X-ray that has penetrated the material.

Figure 8:
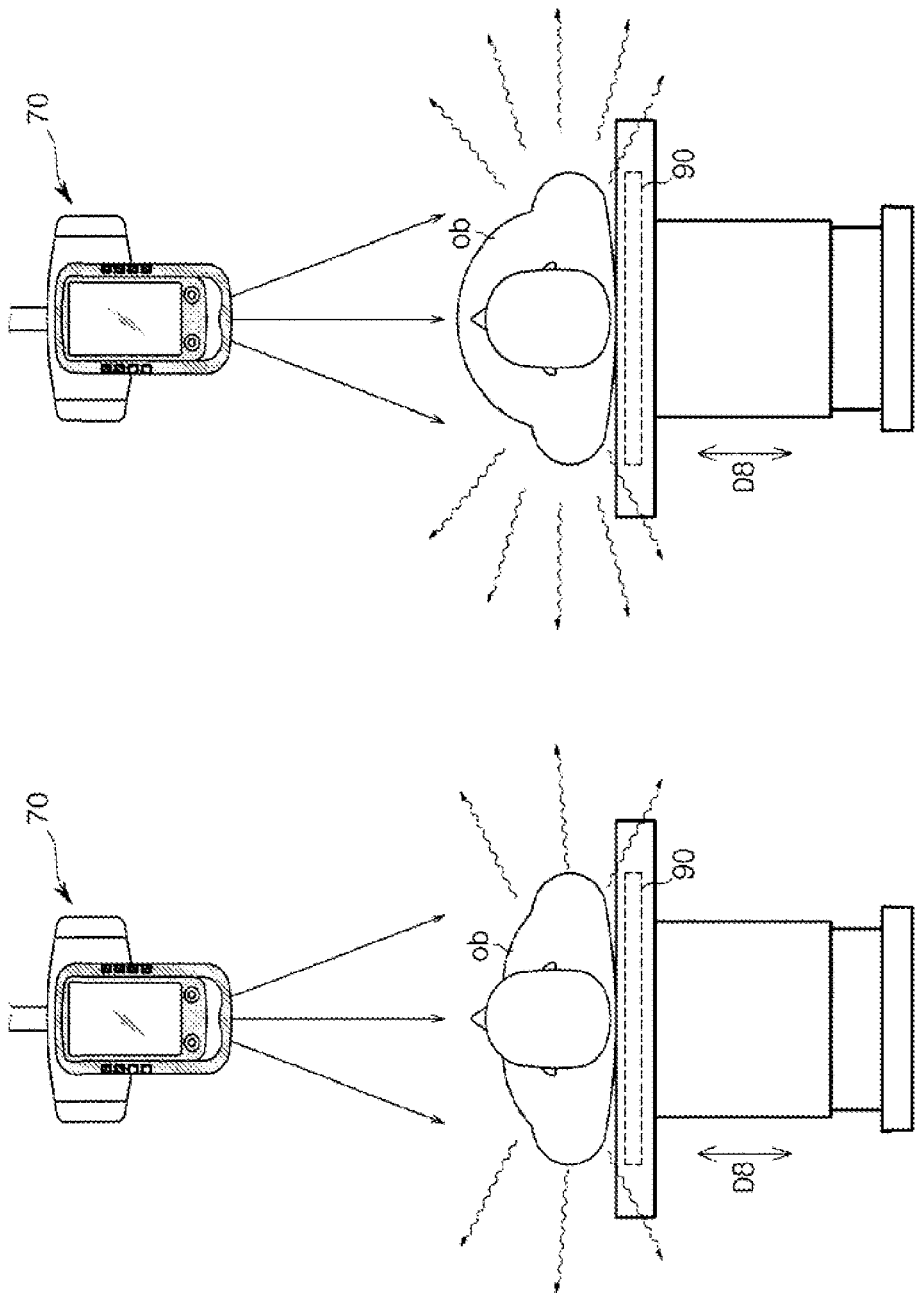
FIG. 8 is an illustration for explaining an attenuation effect depending on thickness of fat.

FIG. 8 is an illustration for explaining an attenuation effect depending on thickness of fat.

Specifically, the illustration on the left shows X-rays being irradiated to a subject that has a normal amount of fat and the illustration on the right shows X-rays being irradiated to a subject that has an amount of fat greater than normal (i.e., an obese subject). As previously mentioned, the thicker the material, the higher the attenuation coefficient, and for a constituent material of the subject, e.g., fat, the thicker the fat is (or the greater the amount of fat), the less the intensity of the X-ray that has penetrated the subject (or the transmitted X-ray).

The degree of obesity as described herein refers to an amount, thickness, or ratio of substances that constitute a target region for X-ray scanning. As described above, a quality of an X-ray image may increase only when an amount of X-ray irradiation is controlled according to ratios of fat, bones, muscles cartilage, etc., that constitute a target region for X-ray scanning. Accordingly, the X-ray imaging apparatus 102 in accordance with the embodiment may determine a degree of obesity, and control an amount of X-ray irradiation based on the determination. This will be described in more detail later.

In FIG. 8, assuming that the X-ray source 70 radiates X-rays with the same intensity at the same energy level, X-ray scattering or absorption occurs more in the right subject (i.e., the obese subject) than in the left subject (i.e., the subject having a normal amount of fat) and accordingly, the X-ray detector 90 for detecting transmitted X-rays may detect less-intense X-rays from the right subject. In other words, if the degree of obesity of the subject is higher, the intensity of the X-rays detected by the X-ray detector 90 may decrease and accordingly, the X-ray image quality obtained by the X-ray imaging apparatus 100 may also degrade.

Accordingly, the controller 500 may control the X-ray source 70 to irradiate X-rays with higher intensity or brilliance or brightness as the degree of obesity of the subject increases. Before this, the table actuator 200 may operate to determine the degree of obesity of the subject.

Figure 9:
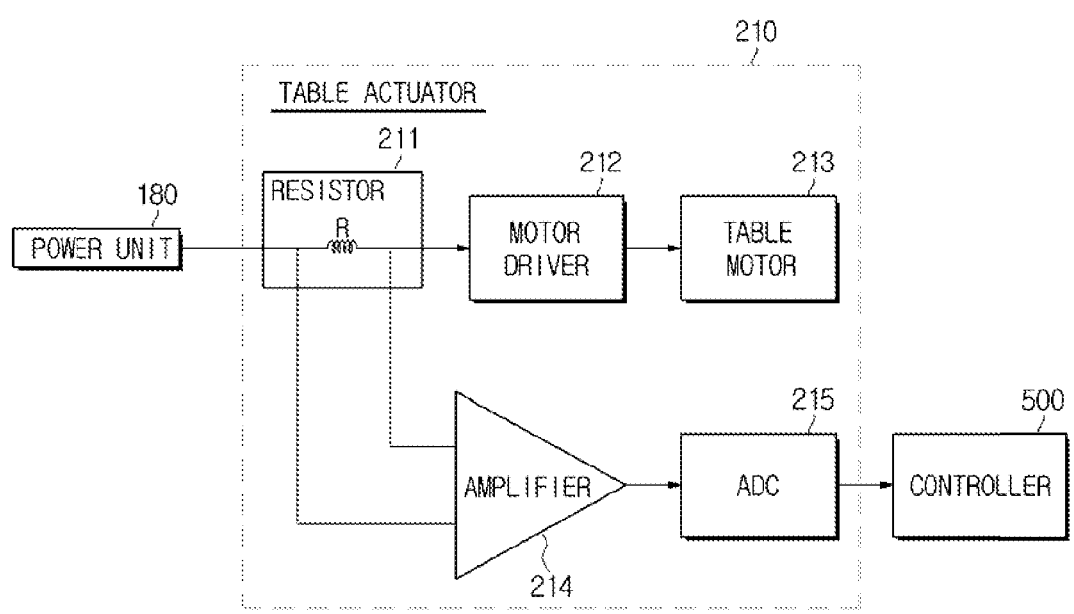
FIG. 9 is a diagram of a table actuator, according to an embodiment of the present disclosure.
Figure 10:
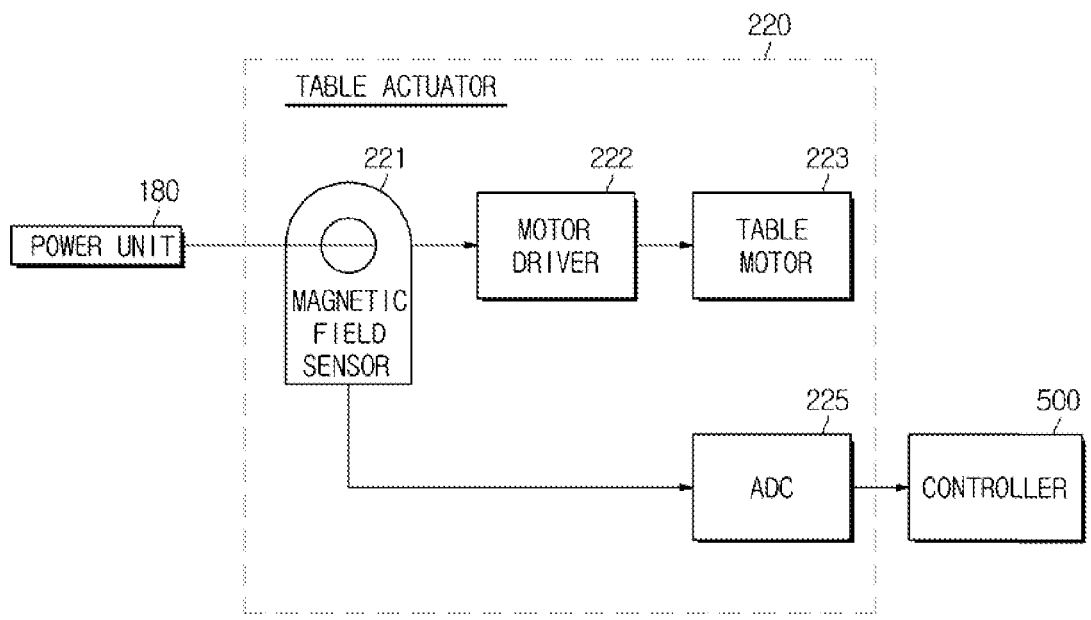
FIG. 10 is a diagram of a table actuator, according to another embodiment of the present disclosure.
Figure 11:
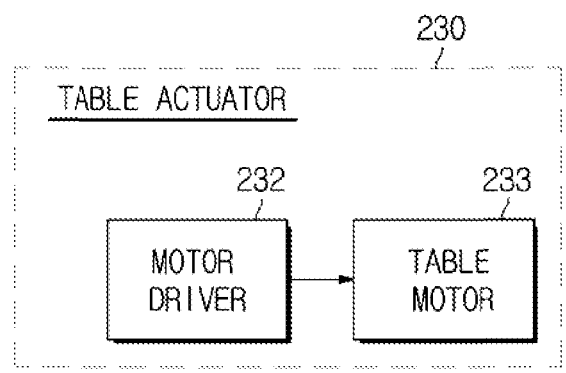
FIG. 11 is a diagram of a table actuator, according to yet another embodiment of the present disclosure.

The table actuator 200 drives a table motor 213 of FIG. 9, 223 of FIG. 10, or 233 of FIG. 11 and shifts the scanning table 10 in the eighth direction D8. The table actuator 200 measures current that flows in the table actuator 200 while the scanning table 10 is being shifted in the eighth direction D8, and forwards the measured current to the controller 500. The table actuator 200 measures the current based on whether the subject is present and how much the subject weighs (i.e., how much load is applied to the table actuator 200). The current corresponds to the force needed to move the table 10.

FIG. 9 is a diagram of a table actuator, according to an embodiment of the present disclosure.

Referring to FIG. 9, the table actuator 210 may include, for example, resistor R 211, amplifier 214, Analog to Digital Converter (ADC) 215 in addition to the motor driver 212 and the table motor 213.

The motor driver 212 drives the table motor 213 with power supplied from the power unit 180. The resistor R 211 is arranged between the power unit 180 and the motor driver 212, which may be a sensing resistor or a shunt resistor. The amplifier 214 is connected across the resistor R 211 to measure a voltage difference across the resistor R 211 or current Im that flows through the resistor R 211, and amplifies the measurement result. The ADC 215 converts an analog current signal delivered from the amplifier 214 to a digital current signal and forwards the digital current signal to the controller 500.

Alternatively, the voltage difference across the resistor R 211 or current Im that flows through the resistor R 211 may be measured using an external measuring device. In an embodiment, the external measuring device may include a device, such as a multimeter, to measure a voltage or current. But it is not limited thereto and the external measuring device may include any device that is able to measure a voltage difference or current.

FIG. 10 is a diagram of a table actuator, according to another embodiment of the present disclosure.

Referring to FIG. 10, the table actuator 220 may include, for example, magnetic field sensor 211 and Analog to Digital Converter (ADC) 225 in addition to the motor driver 222 and the table motor 223.

The motor driver 222 drives the table motor 223 with power supplied from the power unit 180. The magnetic field sensor 221 may be arranged between the power unit 180 and the motor driver 222, which may be a hall sensor. The magnetic field sensor 221 may sense a voltage based on the magnetic flux and accordingly, detect a current Im that flows through the motor driver 222. The ADC 225 converts an analog current signal delivered from the magnetic field sensor 221 to a digital current signal and forwards the digital current signal to the controller 500.

FIG. 11 is a diagram of a table actuator, according to yet another embodiment of the present disclosure.

Referring to FIG. 11, the table actuator 230 may include motor driver 222 and table motor 233. In this case, the motor driver 222 itself contains a current sensor and an ADC, or contains a current sensing circuit including the current sensor and the ADC.

However, the configurations of the table actuator 200 shown in FIGS. 9, 10, and 11 are only examples, and any other configurations of the table actuator 200 may be possible as long as they are able to measure the current that flows through the table actuator 200.

The table actuator 200 shifts the scanning table 10 in the eight direction D8 and measures the current, while there is a subject (i.e., a load). The current measured while there is a subject (i.e., a load) may be called a load current, while the current measured while the scanning table 10 is being shifted without a subject (i.e., a load) may be called a no-load current.

The controller 500 controls general operations of the X-ray imaging apparatus 101.

The controller 500 controls operations of all the components of the X-ray imaging apparatus 101, such as the X-ray source 70, the X-ray detector 90, the table actuator 200, the storage unit 550, the display unit 172, etc.

The controller 500 may generate a control signal to measure a current and send the control signal to the table actuator 200. The controller 500 may receive a current measured by the table actuator 200 and use the current to determine an obese level of the subject.

The controller 500 may calculate an average current from the current received from the table actuator 200, and use the average current to determine how obese is the subject.

FIG. 12 shows plots for explaining how to calculate an average current.

The motor driver 212, 222, or 223 may drive the table motor 213, 223, or 233 with supplied power, and at this time, the analog current flowing through the table actuator 200 may have a form of the graph shown in (a) of FIG. 12. When the table motor 213, 223, or 233 is initiated, an inrush current may be detected.

To reduce an error due to the inrush current, the controller 500 may use the current measured after a predetermined point of time or the current measured during a predetermined period of time T as shown in (b) or (c) of FIG. 12, to determine the degree of obesity.

Specifically, the analog current as shown in (a) of FIG. 12 may be converted to a digital current shown as shown in (b) of FIG. 12, which may then be sent to the controller 500. In other words, the ADC may send the controller 500 the measured current extracted at a predetermined sampling rate.

The controller 500 may calculate an average of the measured current extracted during the predetermined period of time T from time T0 when the table motor 213, 223, or 233 is initiated, using the following equation 2.

$$X_{rms} = \sqrt{\frac{1}{n}(X_1^2 + X_2^2 + \ldots + X_n^2)} \tag{2}$$

where $X_i$ (i=1, 2, ..., n) refers to an extracted measured current, n refers to the number of extraction times, and $X_{rms}$ refers to an average current.

As illustrated in (c) of FIG. 12, assuming that measured currents $X_1, X_2, X_3$, and $X_4$ are extracted at extraction points T1, T2, T3, and T4, respectively, at a sampling rate during a predetermined period of time T, the controller 500 may calculate the average current $X_{rms}$ to be $$X_{rms} = \sqrt{\frac{1}{4}(X_1^2 + X_2^2 + X_3^2 + X_4^2)}$$

using equation 2. When the controller 500 calculates the average current, the load current refers to an average of the measured currents with a load and the no-load current refers to an average of the measured currents without a load.

However, the way of calculating an average current by the controller 500 is not limited thereto. For example, the controller 500 may determine a median value of the extracted measured currents arranged in the increasing (or decreasing) order to be an average current, or may determine the most frequently extracted one of the extracted measured currents to be an average current. In another example, if at least one of the extracted measured currents is greater or less than the other measured currents by more than predetermined level, the controller 500 may determine the at least one extracted measured current as an error and leave it out of calculation of an average current. In yet another example, in calculating an average current, the minimum and maximum measured currents among the extracted measured currents may be determined as errors, and may be left out of calculation of the average current. Moreover, the controller 500 may calculate an average current in various ways of averaging, without limiting the method of averaging to the aforementioned methods.

The controller 500 uses the load current measured or calculated to determine a degree of obesity of the subject. The controller 500 may determine a degree of obesity of the subject by comparing the load current with a predetermined threshold current, or by comparing a weight of the subject calculated from the load current with a predetermined threshold weight. The predetermined threshold current refers to a current that corresponds to a threshold weight for determining a degree of obesity, and at least one threshold current may be set in advance and stored in the storage unit 550. Likewise, at least one threshold weight may be set in advance and stored in the storage unit 550.

Figure 13:
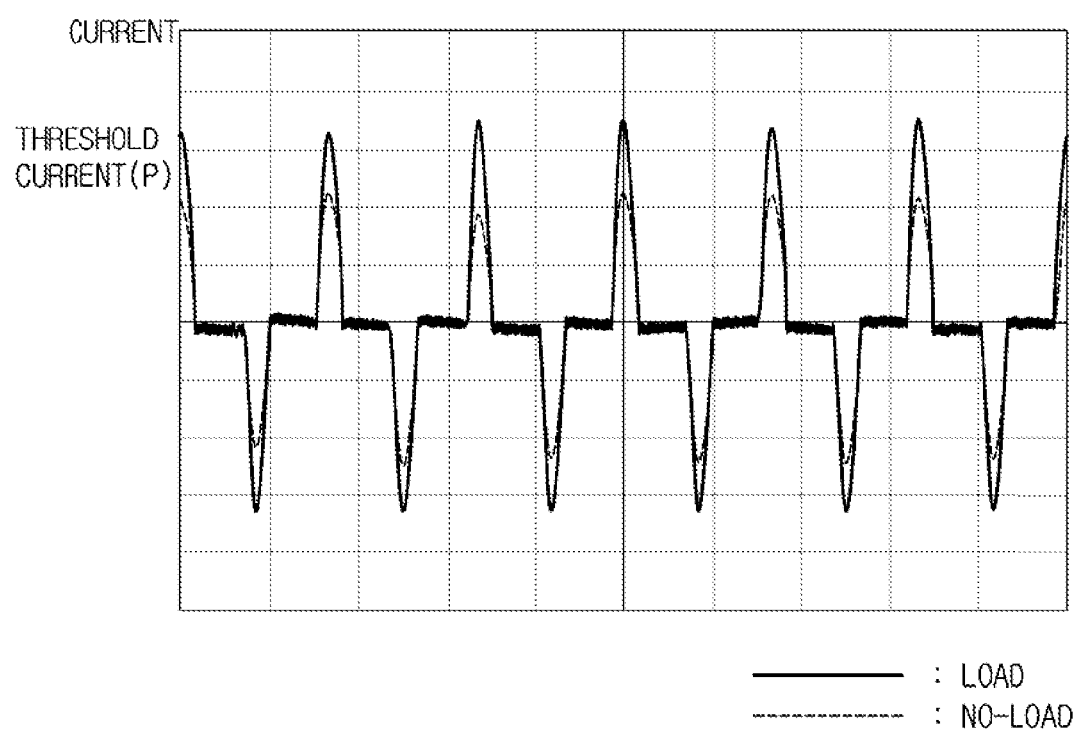
FIGS. 13 and 14 are graphs for explaining how to determine degree of obesity based on a threshold current.
Figure 14:
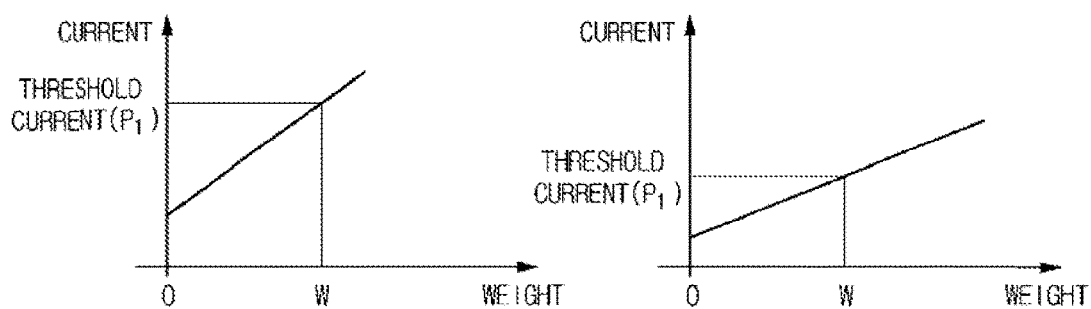

FIGS. 13 and 14 are graphs for explaining how to determine degree of obesity based on a threshold current.

Referring to FIG. 13, a single threshold current P may be set. The single threshold current P is a current that corresponds to a threshold weight (e.g., 130 Kg) for determining a degree of obesity, which is set greater than a no-load current. Thus, the controller 500 compares the load current with the threshold current P, and determines that the subject is obese if the load current is greater than the threshold current P. Since the load current is greater than the threshold current in FIG. 13, the controller 500 determines that the subject is obese.

There may be multiple threshold currents set. The multiple threshold currents are currents that correspond to multiple threshold weights (e.g., 130 kg, 140 kg, and 150 kg), which are set greater than no-load currents, and the controller 500 may use the multiple threshold currents that increase stepwise to determine a degree of obesity of the subject.

The threshold current may be set differently depending on the shifting direction of the scanning table 10.

The graph on the left side of FIG. 14 represents no-load current or load current measured (or calculated) based on the weight of the subject while the scanning table 10 is being shifted in the opposite direction of the gravity, i.e., in the upward direction, and the graph on the right side of FIG. 14 represents no-load current or load current measured (or calculated) based on the weight of the subject while the scanning table 10 is being shifted in the gravity direction, i.e., in the downward direction. In this regard, the current for zero weight is the no-load current, and the current for the weight greater than zero is the load current.

Due to gravity, the table actuator 200 is loaded heavier and thus the current consumption increases while the scanning table 10 is shifted upward as compared with when the scanning table 10 is shifted downward. Accordingly, even the no-load current is measured (or calculated) to be higher and thus the graph is sloped highly while the scanning table 10 is being shifted upward.

Thus, even for the same threshold weight W, the threshold current for an occasion where the scanning table 10 is moved upward P1 and the threshold current for an occasion where the scanning table 10 is moved downward P2 may be differently set. That is, the threshold current for upward movement P1 may be set to be higher than the threshold current for downward movement P2.

Additionally, a motor may be installed in the scanning table 10 to move the scanning table 10 horizontally. Accordingly, the scanning table 10 may be moved by the motor in the horizontal direction. When the scanning table 10 is moved in the horizontal direction, a degree of obesity may be determined based on current consumption because the weight is proportional to the current load. A threshold current for horizontal movement P3 of the scanning table 10 may be differently set from the currents for upward and downward movements P1 and P2.

Furthermore, the controller 500 may determine a degree of obesity of the subject by comparing the weight of the subject calculated from the load current with the predetermined threshold weight. For this, the storage 550 may store data relating to at least one threshold weight, and graphs of FIG. 14, i.e., relationships between weight and current.

Specifically, the controller 500 may calculate a weight of the subject from the load current using the relationship between weight and current, may determine a degree of obesity of the subject by comparing the calculated weight with a threshold weight (e.g., 130 kg) or determine the degree of obesity of the subject by comparing the calculated weight with multiple threshold weights that increase stepwise (e.g., 130 kg, 140 kg, and 150 kg).

An acceleration sensor may be installed in the scanning table 10 or the X-ray detector. Instantaneous acceleration of the scanning table 10 is different for a weight of the subject, while the scanning table 10 is moving in the horizontal, up, or down direction. Furthermore, even if the scanning table 10 is moving in the same direction and the motor is driven at the same power, instantaneous acceleration decreases as the weight of the subject increases. That is, the weight of the subject and instantaneous acceleration of the scanning table 10 are inversely proportional to each other. Accordingly, the controller 500 may measure instantaneous acceleration of the scanning table 10 with the acceleration sensor, and determine a degree of obesity of the subject based on the measured result. Data of instantaneous acceleration for a weight of the subject may be pre-calculated for each direction and may be stored in the storage unit 550. The controller 500 may use the data stored in the storage unit 550, to calculate a weight that corresponds to the measured instantaneous acceleration.

The controller 500 may control the tube voltage or the tube current of the X-ray tube 71 based on the determination a degree of obesity of the subject, thus controlling the intensity of the X-ray to be radiated from the X-ray source 70. An irradiation level of X-rays, as will be described below, refers to an amount or intensity (brilliance or brightness) of irradiation of X-rays.

The controller 500 controls the X-ray source 70 to irradiate higher intense X-rays for an obese subject compared with a subject having a normal amount of fat. The controller 500 controls the X-ray source 70 to irradiate higher intense X-rays as the degree of obesity of the subject gets higher. In this regard, intensities of the X-ray for the subject having a normal amount of fat and the obese subject may be set and stored in advance, and likewise, irradiation levels of the X-ray for sections to be scanned may be set and stored in advance, in for example, a table, based on the degree of obesity of the subject.

The controller 500 may receive the X-ray detected from the X-ray detector 90 and create a projection image, i.e., an X-ray image of the subject based on the intensity of the X-ray.

Such an X-ray image may be displayed through the display unit 172. Since the irradiation level of the X-ray is controlled based on the degree of obesity of the subject, the quality of the X-ray image to be displayed through the display unit 172 may be improved.

The storage unit 550 stores data and programs for operation of the X-ray imaging apparatus 101.

For example, for comparison of the load current and the threshold current, the storage unit 550 may store at least one threshold current set in advance. Alternatively, for comparison of the load current and the threshold weight, the storage unit 550 may store data relating to graphs of relationships between weight and current while the scanning table 10 is being shifted upward and while the scanning table 10 is being shifted downward. The storage unit 550 may store at least one predetermined threshold weight, and X-ray irradiation intensities for a subject having a normal amount of fat and an obese subject per section to be imaged, and X-ray irradiation intensities per section to be imaged based on how much the subject is obese. Furthermore, the storage unit 550 may also store programs to determine a degree of obesity based on the threshold current or the threshold weight. The storage unit 550 may include storage media in at least one of flash memory, hard disk, multimedia card micro type memory, card type memory (e.g., SD or XD memory), Random Access Memory (RAM), Static Random Access Memory (SRAM), Read-Only Memory (ROM), Electrically Erasable Programmable Read-Only Memory (EEPROM), Programmable Read-Only Memory (PROM), magnetic memory, magnetic disk, and optical disk. However, the storage media is not limited thereto, but may be implemented in any other form known in the art. The X-ray imaging apparatus 102 may operate a web storage that serves as a memory 150 on the Internet.

Additionally, a degree of obesity predicted with the aforementioned program and an actual degree of obesity of the subject may be stored in the storage unit 550. The controller 500 may then compare the degree of obesity predicted by the program and the actual degree of obesity of the subject, and perform a process of correcting the error to update the program. The controller 50 may more accurately determine the degree of obesity of the subject by continuously updating the program.

Figure 15:
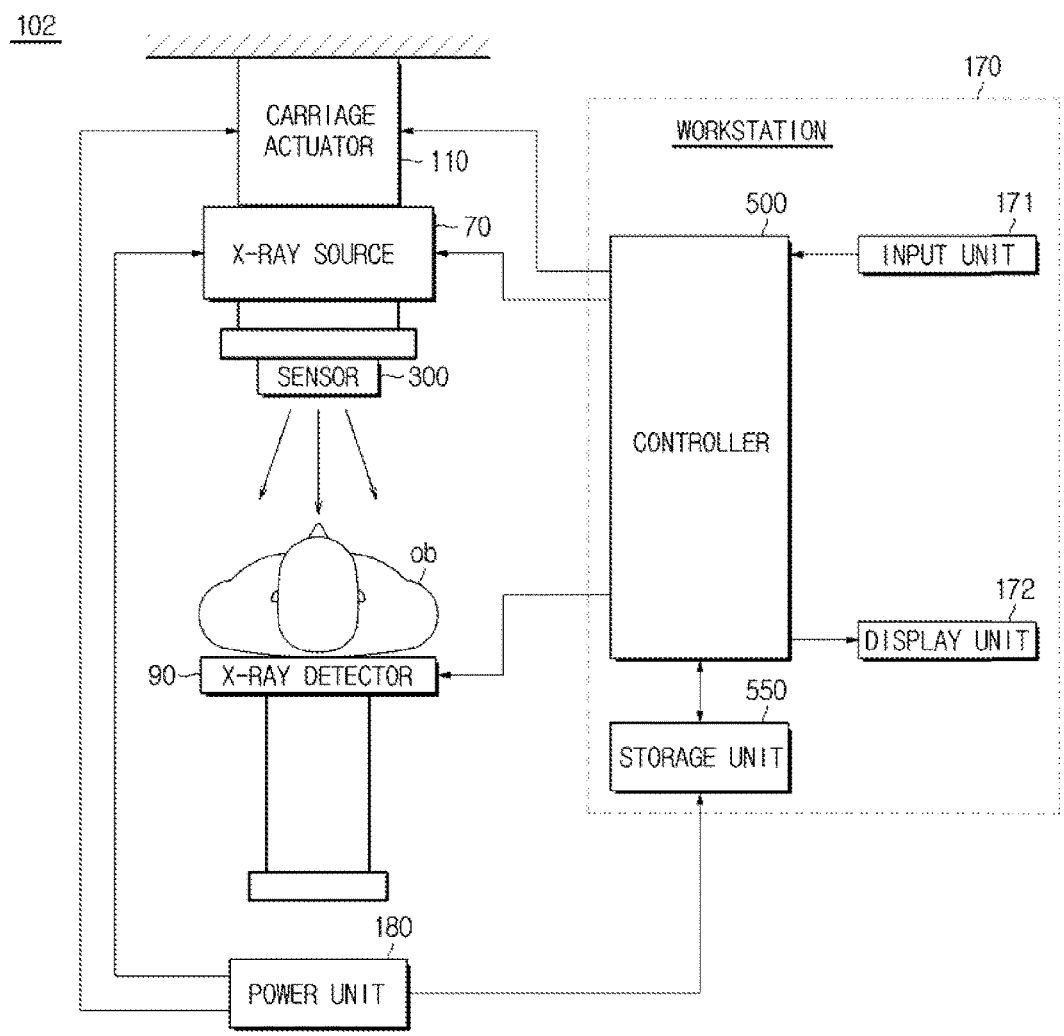
FIG. 15 is a control block diagram of an X-ray imaging apparatus, according to another embodiment of the present disclosure.

FIG. 15 is a control block diagram of an X-ray imaging apparatus, according to another embodiment of the present disclosure.

Referring to FIG. 15, the X-ray imaging apparatus 102 may include, for example, power unit 180, X-ray source 70, X-ray detector 90, carriage actuator 110, sensor 300, controller 500, storage unit 550, input unit 171, and display unit 172. The same components of the X-ray imaging apparatus 102 as described above will be omitted herein.

The sensor 300 is mounted on the X-ray source 70 to detect a distance to the subject from the X-ray source 70 or obtain an image of the subject. The sensor 300 may include at least one of a proximity sensor and an image sensor.

For example, the sensor 300 may be a proximity sensor (see 51 of FIG. 16) to detect a distance between the X-ray source 70 and the subject. The proximity sensor 51 may have a form of a photo sensor (e.g., infrared sensor, PSD sensor, CCD sensor, etc.) or a Radio Frequency (RF) sensor.

For example, the X-ray imaging apparatus 102 may detect a distance between the X-ray source 70 and the subject by adjusting the measuring angle of the proximity sensor S1. In another example, if the proximity sensor S1 is mounted on the X-ray source 70, the X-ray imaging apparatus 102 may detect the distance between the X-ray source 70 and the subject as the X-ray source 70 is moved.

Figure 16:
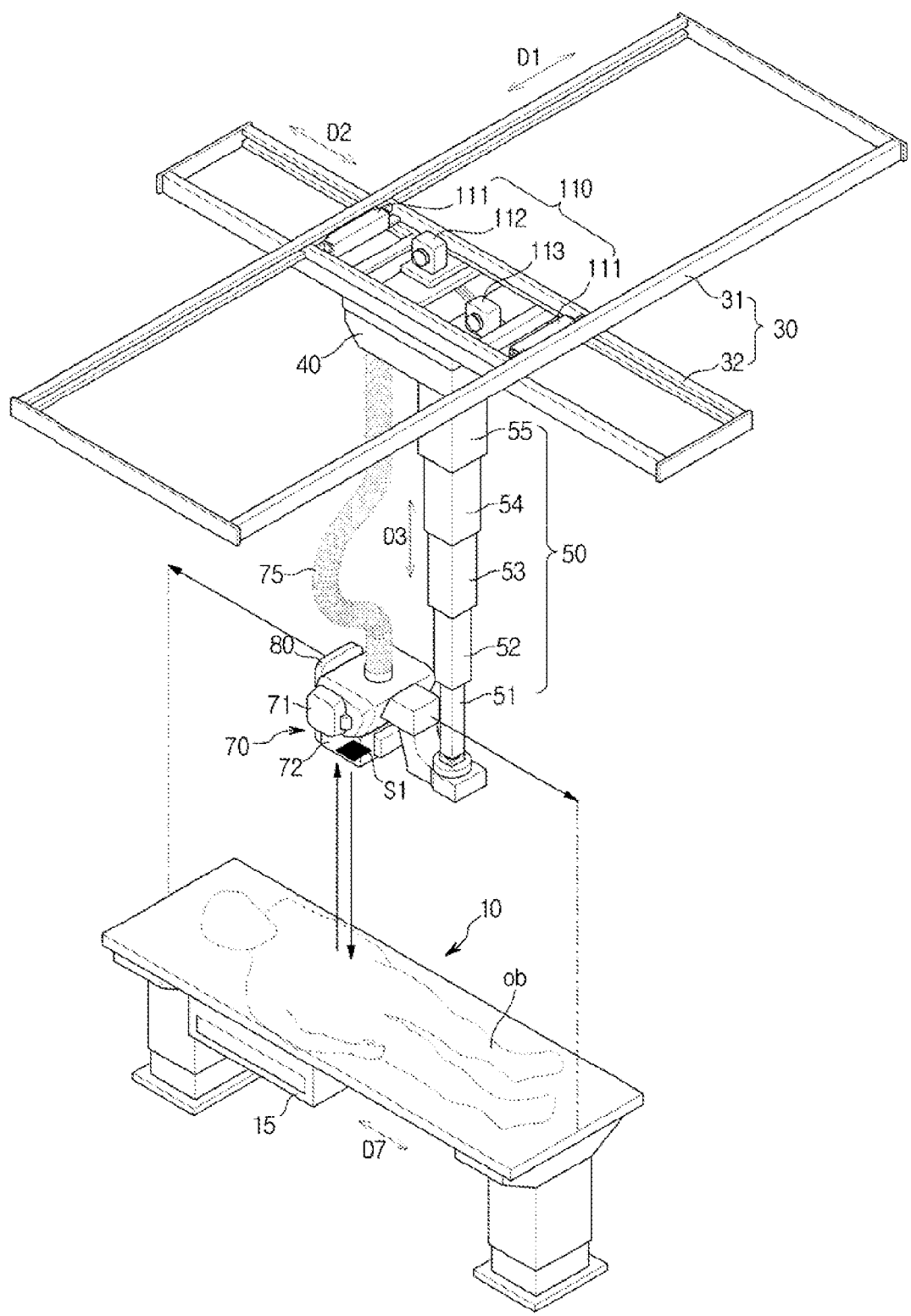
FIG. 16 is an illustration for explaining distance detection with a proximity sensor.

FIG. 16 is an illustration for explaining distance detection with a proximity sensor.

Referring to FIG. 16, the proximity sensor S1 may be mounted on a bottom part of the X-ray source 70, e.g., around the collimator 72. Under control of the controller 500, the X-ray source 70 is shifted in the direction of the length of the scanning table 10, and the proximity sensor S1 detects a distance to the scanning table 10 or the subject (or object ob) while the X-ray source 70 is being shifted. The proximity sensor S1 delivers an output value of the distance to the controller 500 and the controller 500 then detects or determines a height and volume of the subject and determines whether or how much the subject is obese based on the detected height and volume.

Figure 17:
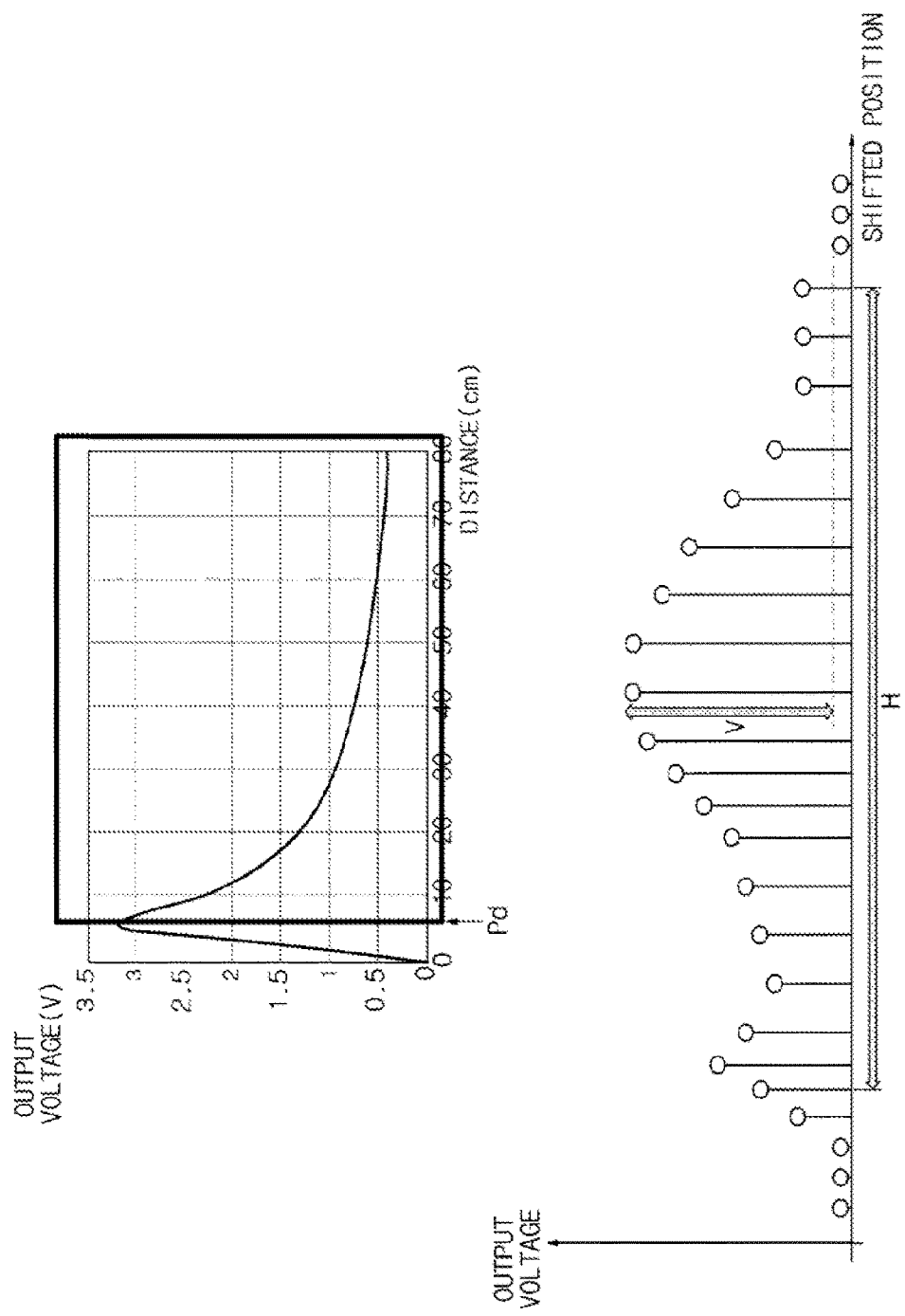
FIG. 17 shows graphs for explaining how to detect a height and volume of a subject using outputs of a proximity sensor.

FIG. 17 shows graphs for explaining how to detect a height and volume of a subject using outputs of a proximity sensor.

The graph in the upper part of FIG. 17 represents output voltages of the proximity sensor S1 according to the distance. When an object is within a predetermined distance Pd from the proximity sensor S1, the output voltage of the proximity sensor S1 increases rapidly as a distance to the object gets farther. On the contrary, when the object is not within the predetermined distance Pd from the proximity sensor S1, the output voltage of the proximity sensor S1 decreases as a distance to the object gets farther. That is, the output voltage of the proximity sensor S1 increases rapidly in proportion to the distance to the object within the predetermined distance Pd while decreasing in inverse proportion to the distance to the object after the predetermined distance Pd. Accordingly, with the X-ray source 70 and the proximity sensor S1 set up to have a distance to the subject farther than the predetermined distance Pd, a height and volume of the subject may be detected using the curve after the predetermined distance Pd, i.e., the inverse proportional curve.

The proximity sensor S1 sends the controller 500 the output voltage being output while the X-ray source 70 is moving, the output voltage having the form of a graph shown in the lower part of FIG. 17. As discussed above, since the output voltage of the proximity sensor S1 is inversely proportional to the distance, the output voltage has the highest value near the abdomen while having the lowest value near the scanning table 10.

Accordingly, the controller 500 converts the highest output voltage and the lowest output voltage to a distance to the subject and a distance to the scanning table 10, respectively, according to the upper graph of FIG. 17, and obtains the thickness of the abdomen to be the difference between those converted distances. The thickness of the abdomen may be or represent a volume V of the subject (that is, for example, a 180 degree rotated solid object having radiuses V). Furthermore, the controller 500 may obtain the height H of the subject, exclusive of both ends that remain at the lowest output voltage in the lower graph of FIG. 17.

The controller 500 uses the obtained volume V and height H to determine whether or how obese is the subject. How to determine how much the subject is obese based on volume V and height H may use a known technology, thus the description of which will be omitted herein.

If the sensor 300 is the proximity sensor S1, the controller 500 generates a control signal to drive the carriage actuator 110, which in turn shifts the X-ray source 70 in the direction of the length of the scanning table 10. The carriage actuator 110 is to move the X-ray source 70, and may hereinafter be also referred to as a source actuator 110. The storage unit 550 may store data relating to the relationship between the output voltage and the distance as shown in the upper graph of FIG. 17, and store a program to obtain the volume V and height H using the data.

The sensor 300 may be an image sensor, such as a camera for detecting a distance to the subject or obtain an image of the subject. The sensor 300 may be at least one image sensor. For example, the sensor 300 may be a single image sensor (see image sensor S2 of FIG. 18) to obtain an image of the subject. Alternatively, the sensor 300 may be multiple image sensors (see image sensors S21 and S22 of FIG. 20) to detect the distance to the subject.

Figure 18:
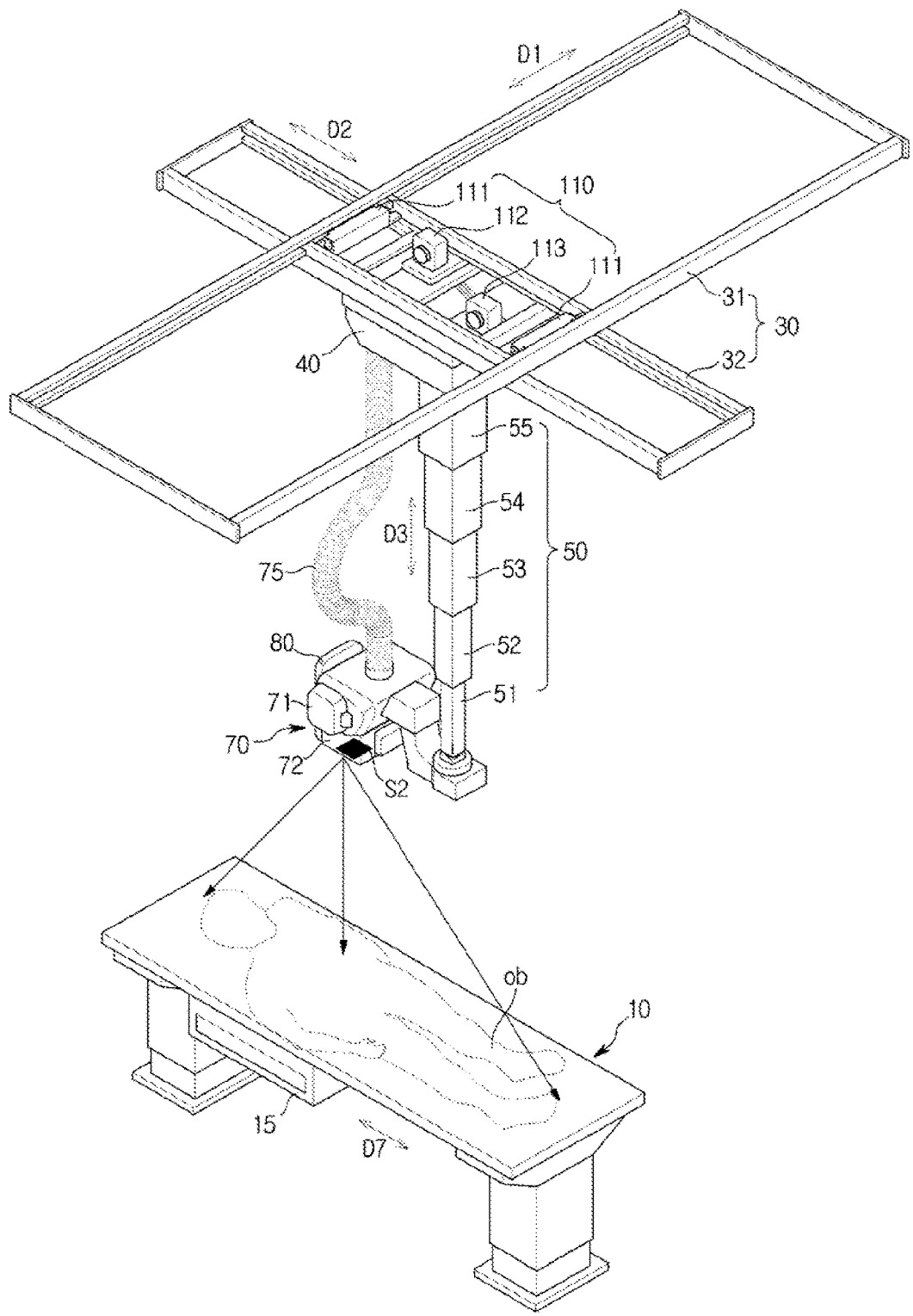
FIG. 18 is an illustration for explaining how to obtain an image with a single image sensor.

FIG. 18 is an illustration for explaining how to obtain an image with a single image sensor. Referring to FIG. 18, an image sensor S2 may be mounted on a bottom part of the X-ray source 70, e.g., around the collimator 72, to obtain an image of the subject from above. That is, the image sensor S2 obtains an image of the upper part of the subject. The image sensor S2 delivers the output value to the controller 500, and the controller 500 then detects a height and volume of the subject and determines a degree of obesity of the subject.

Figure 19:
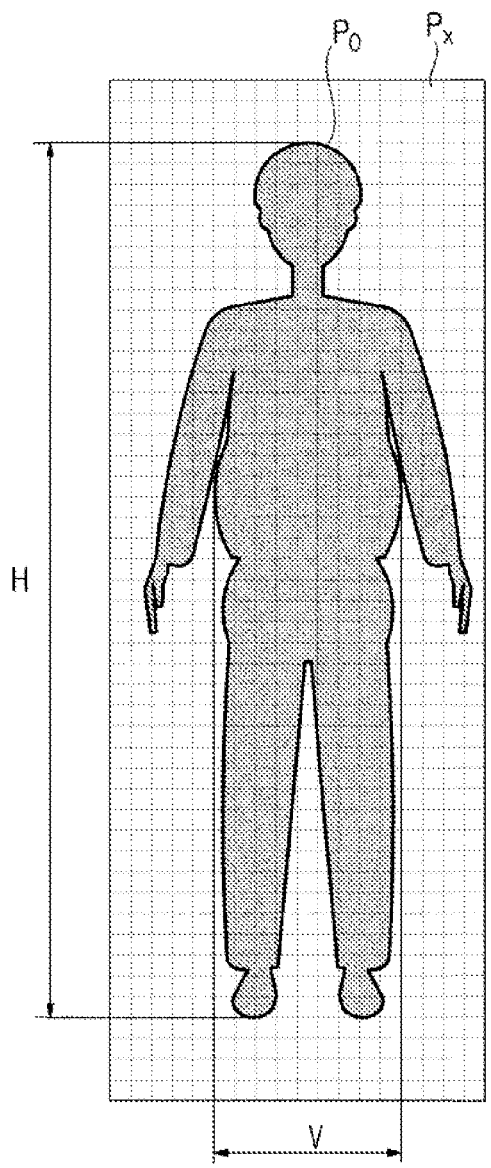
FIG. 19 is an illustration for explaining how to detect a height and volume of a subject using output values of an image sensor.

FIG. 19 is an illustration for explaining how to detect a height and volume of a subject using output values of an image sensor.

The image sensor S2 may obtain an image of the upper part of the subject, as illustrated in FIG. 19. Output values of the image sensor S2 are pixel values Px of the image, which drastically change on the boundary between where the subject is present and where the subject is not present, i.e., on the outline Po of the subject. Thus, the controller 500 detects the outline Po of the subject from the changes in pixel value, and obtains a width V of the abdomen and height H of the subject. The width of the abdomen may be or represent a volume V of the subject (that is, for example, a 180 degree rotated solid object having diameter V). The controller 500 uses the obtained volume V and height H to determine a degree of obesity of the subject.

When the sensor 300 is a single image sensor S2, the storage unit 550 may store data relating to an image obtained by the image sensor S2 or pixel values Px of the image output from the image sensor S2, a program to detect the outline Po of the subject using the data, a program to obtain the volume V and height H from the detected outline Po, etc.

Figure 20:
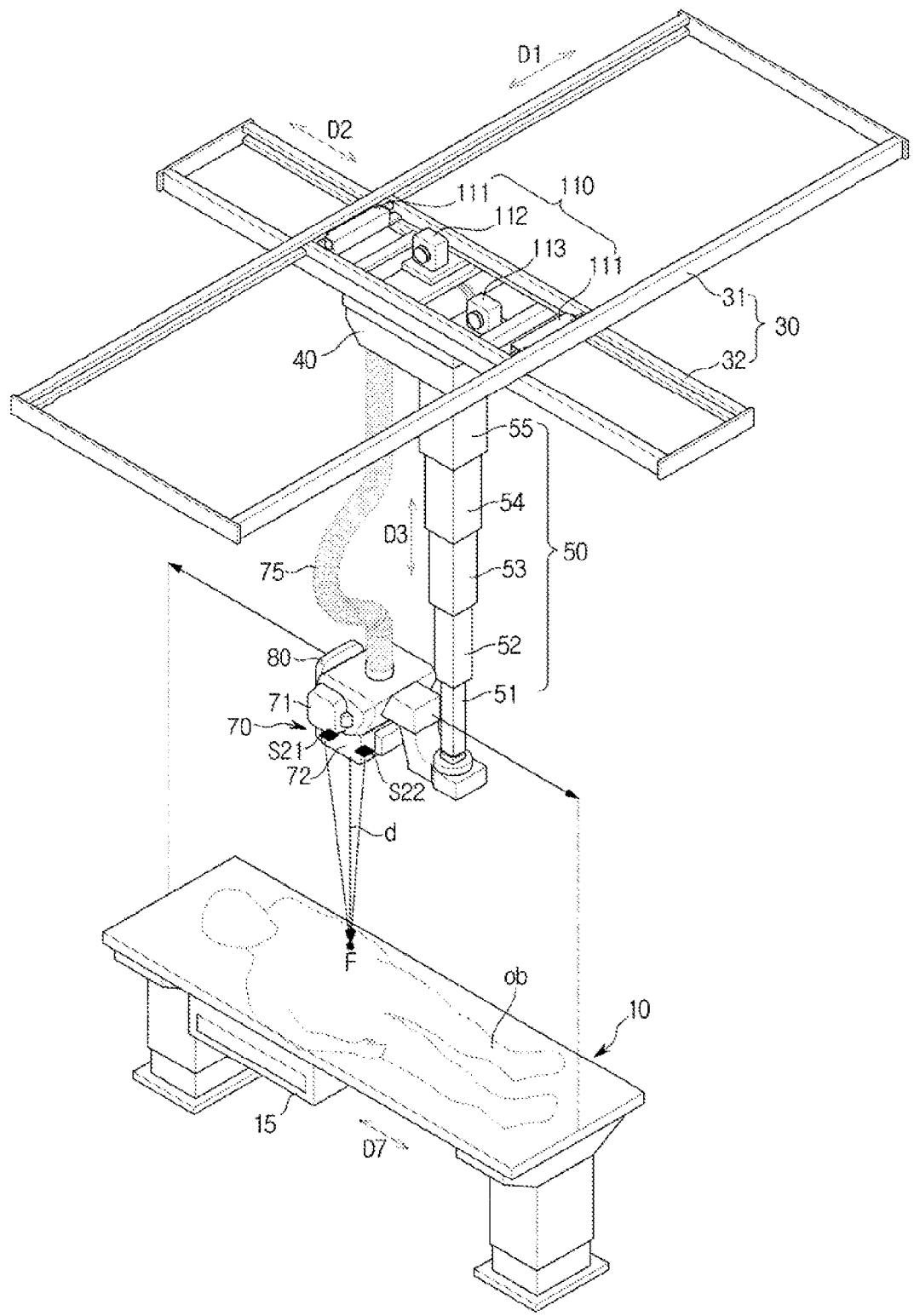
FIG. 20 is an illustration for explaining distance detection with multiple image sensors.

FIG. 20 is an illustration for explaining distance detection with multiple image sensors.

Referring to FIG. 20, multiple image sensors S21 and S22 may be mounted on a bottom part of the X-ray source 70, e.g., around the collimator 72. Angles of the multiple image sensors S21 and S22 may be controlled to have the same focal point (e.g., focal point F). Under control of the controller 500, the X-ray source 70 is shifted in the direction of the length of the scanning table 10, and the multiple image sensors S21 and S22 moves the focal point F on the surface of the scanning table 10 or the subject (or object ob) as the X-ray source 70 is shifted. While the focal point F is moving, output values of the image sensors S21 and S22 are delivered to the controller 500, which in turn uses them to calculate a distance to the scanning table 10 or the subject ob. The output values of the image sensors S21 and S22 may be angles for the focal point F. Furthermore, the controller 500 detects a height and volume of the subject from the calculated distance and determines a degree of obesity of the subject.

Figure 21:
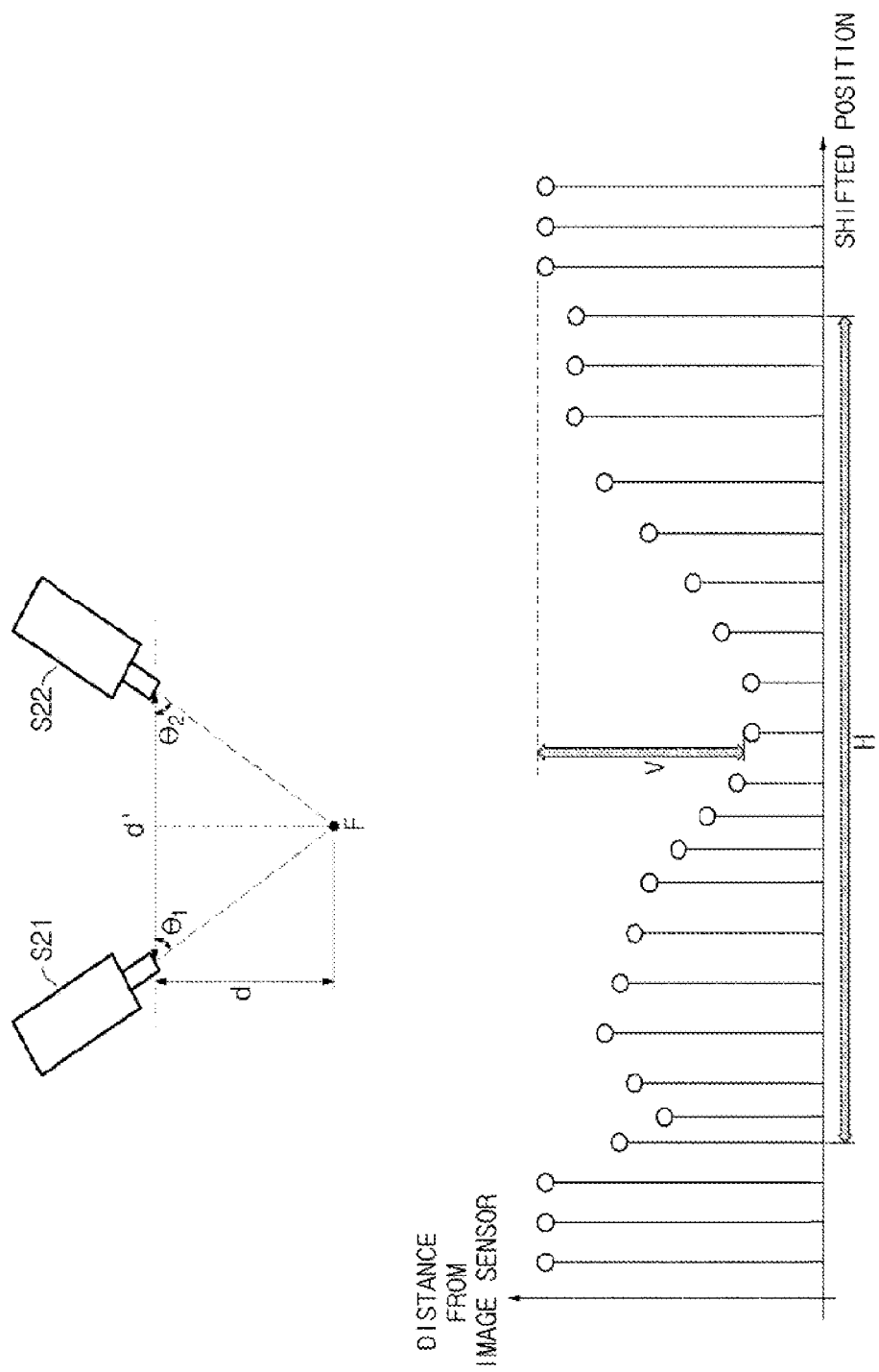
FIG. 21 shows diagrams for explaining how to detect a height and volume of a subject using output values of multiple image sensors.

FIG. 21 shows diagrams for explaining how to detect a height and volume of a subject using output values of multiple image sensors.

As shown in the upper illustration of FIG. 21, when a distance between the two image sensors S21 and S22 is d' and output values (i.e., angles) of the image sensors S21 and S22 for the focal point F are $\theta_1$ and $\theta_2$, respectively, a distance d to the subject from the image sensors S21 and S22 may be expressed in the following equation 3.

$$d = \frac{d'}{\tan(90° - \theta_1) + \tan(90° - \theta_2)}$$

The controller 500 may use the output values of the image sensors S21 and S22 and equation 3 to calculate the distance d to the scanning table 10 or the subject ob from the image sensors S21 and S22.

As mentioned above, the image sensors S21 and S22 shift the focal point F and deliver their output values to the controller 500 while the X-ray source 70 is moving. The controller 500 may calculate the distance d to the scanning table 10 or the subject ob from the image sensors S21 and S22 for the shifted location of the focal point F, the distance having a form of a graph shown in the lower part of FIG. 21. That is, the distance d from the image sensors S21 and S22 has the smallest value at somewhere around the abdomen of the subject ob while having the greatest value at somewhere around the scanning table 10.

Thus, the controller 500 may obtain the difference between the greatest and smallest values of the distance d as the thickness of the abdomen of the subject ob. The thickness of the abdomen may be ore represent or be used to derive a volume V of the subject. Furthermore, the controller 500 may obtain the height H of the subject, exclusive of both ends that remain to have the greatest value in the lower graph of FIG. 21. The controller 500 uses the obtained volume V and height H to determine a degree of obesity of the subject.

If the sensor 300 has multiple image sensors S21 and S22, the controller 500 generates a control signal to drive the carriage actuator 110 (or a source actuator), which in turn shifts the X-ray source 70 in the direction of length of the scanning table 10. The storage unit 550 may store the distance d' between the image sensors S21 and S22, a program for calculating the distance d from the image sensors S21 and S22 based on the output values of the image sensors S21 and S22, a program for obtaining the volume V and height H of the subject with the calculated distance d, etc.

Although FIGS. 16 to 21 illustrates the embodiments where the sensor 300 only includes the proximity sensor or the image sensor, any other types of sensors may be used for the sensor 300 in other embodiments and a combination of the proximity sensor and the image sensor may also be used.

In still another embodiment, degree of obesity of the subject may be determined using techniques such as near-infrared interactance, dual energy X-ray absorptiometry, bioelectrical impedance analysis, body average density measurement, anthropometric methods, skinfold methods, ultrasound measurement, or using body mass index (BMI) measurements or any other degree of obesity measurement technique, whether currently known or unknown. The determined degree of obesity data may then be input to the controller 500 either electronically by wired or wireless transmission or by manually inputting the data using operation unit 80 or input unit 171. Then, based on a determination of whether and how much the subject is obese using the degree of obesity data, the controller 500 may then control the intensity of the X-ray to be radiated by the X-ray source 70.

Figure 22:
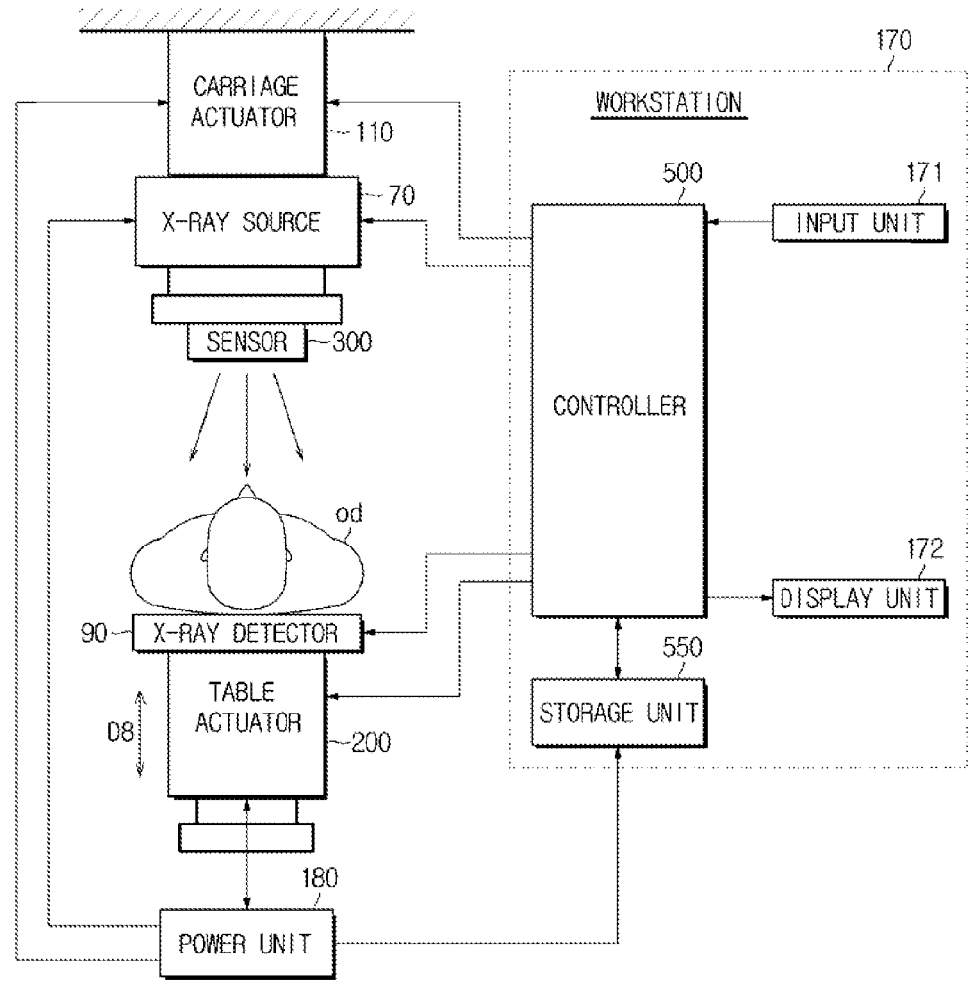
FIG. 22 is a control block diagram of an X-ray imaging apparatus, according to yet another embodiment of the present disclosure.

FIG. 22 is a control block diagram of an X-ray imaging apparatus, according to yet another embodiment of the present disclosure.

Referring to FIG. 22, the X-ray imaging apparatus 103 may include, for example, power unit 180, X-ray source 70, X-ray detector 90, table actuator 200, carriage actuator 110, sensor 300, controller 500, storage unit 550, input unit 171, and display unit 172. The same components of the X-ray imaging apparatus 103 as described above in connection with FIG. 4 or FIG. 16 will be omitted herein.

The sensor 300 may be installed in or on the X-ray source 70 and may include at least one of a proximity sensor and an image sensor. The sensor 300 may include the proximity sensor only, the image sensor only, or a combination of the proximity sensor and the image sensor. If the sensor 300 includes the image sensor, the image sensor may be a single sensor or may include multiple image sensors.

If the sensor 300 includes the proximity sensor or multiple image sensors, the controller 300 drives the carriage actuator 110, which in turn shifts the X-ray source 70 (i.e., in the direction of the length of the scanning table 10), and receives output value(s) of the proximity sensor or multiple image sensors while the X-ray source 70 is being shifted.

If the sensor 300 includes a single image sensor, the controller 300 drives the carriage actuator 110 to have the X-ray source 70 positioned somewhere above the subject, and receives an output value of the single image sensor.

The controller 300 uses the output value to detect a height and volume of the subject.

If the controller 500 receives an output value of the proximity sensor, the controller 500 converts the highest output voltage and the lowest output voltage to a distance to the subject and a distance to the scanning table 10, respectively, according to the upper graph of FIG. 17, and obtains the thickness (or volume) of the abdomen of the subject to be the difference between those converted distances. Furthermore, the controller 500 may obtain the height H of the subject, exclusive of both ends that remain at the lowest output voltage in the lower graph of FIG. 17.

If the controller 500 receives pixel values Px of an image from the image sensor, the controller 500 detects the outline Po of the subject from changes in pixel values, and obtains the volume V and height H of the subject based on the detected outline Po.

If the controller 500 receives an angle of an image sensor, the controller 500 calculates a distance to the scanning table 10 or to the subject using equation 3, and obtains a difference between the greatest value and the smallest value among the calculated distances as a thickness (or volume V) of the abdomen of the subject. Furthermore, the controller 500 may obtain the height H of the subject, exclusive of both ends that remain to have the greatest value in the lower graph of FIG. 21.

The controller 500 generates a control signal to drive the table actuator 200, and the table actuator 200 measures a load current while moving the scanning table 10 in any of the eight directions D8 according to the control signal. The controller 500 receives the load current, and calculates a weight W of the subject from the load current using the graph of relationships between weight and current as shown in FIG. 14.

In another example, the controller 500 may detect a voltage or current (or resistance), which is proportional to a weight W of the subject using a piezoelectric sensor, and calculate the weight W of the subject using the detection result. There may be other various ways of calculating a weight W of the subject that may also be used.

The controller 500 uses the obtained volume V, height H, and weight W to determine a degree of obesity of the subject. How to determine a degree of obesity of the subject based on the volume V, height H, and weight W may use a known technology, thus the description of which will be omitted herein.

The controller 500 may control the tube voltage or the tube current of the X-ray tube 71 based on the determination of the degree of obesity, thus controlling the irradiation level of the X-ray to be radiated from the X-ray source 70.

The X-ray imaging apparatus for determining a degree of obesity of the subject has thus far been described in connection with the illustrated control block diagram. In the following, a method for controlling the X-ray imaging apparatus will be described in connection with some given flowcharts.

Figure 23:
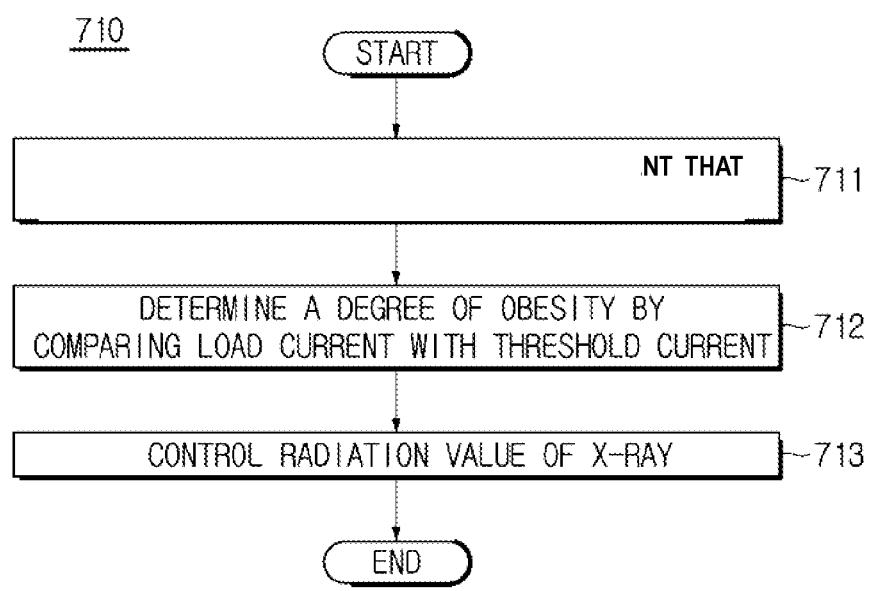
FIG. 23 is a flowchart illustrating a method for controlling an X-ray imaging apparatus, according to an embodiment of the present disclosure.

FIG. 23 is a flowchart illustrating a method for controlling an X-ray imaging apparatus, according to an embodiment of the present disclosure.

Referring to FIG. 23, the table actuator 200 drives a table motor under control of the controller 500, and measures a load current that flows through the table actuator 200 while the table motor is driven, in operation 711.

With a subject lying on the scanning table 10, the table motor is driven under control of the controller 500, and accordingly, the scanning table 10 is shifted in the eighth direction D8, i.e., upward or downward. The table actuator 200 may include a current sensor, magnetic sensor, current sensing circuit, or the like, to measure a current (i.e., a load current) that flows through the table actuator 200 while the table actuator 200 is being shifted, and delivers the current to the controller 500.

The controller 500 determines a degree of obesity of the subject by comparing the load current with at least one predetermined threshold current, in operation 712.

The controller 500 may convert the load current received into an average current form. In addition, if a single threshold current is set, the controller 500 may determine a degree of obesity of the subject by comparing the load current with the single threshold current, and if multiple threshold currents are set, the controller 500 may determine a degree of obesity of the subject by comparing the load current with the multiple threshold currents.

Based on the determination of a degree of obesity of the subject, the controller 500 controls the intensity of the X-ray to be radiated by the X-ray source 70, in operation 713.

If it is determined that the subject is obese, the controller 500 controls higher intense X-ray to be irradiated as compared with a subject having a normal amount of fat. Furthermore, the controller 500 controls higher intense X-ray to be irradiated as the degree of obesity of the subject gets higher. In this regard, intensities of the X-ray for the subject having a normal amount of fat and the obese subject may be set and stored in advance, and likewise, intensities of the X-ray for sections to be scanned may be set and stored in advance based on the degree of obesity of the subject.

Figure 24:
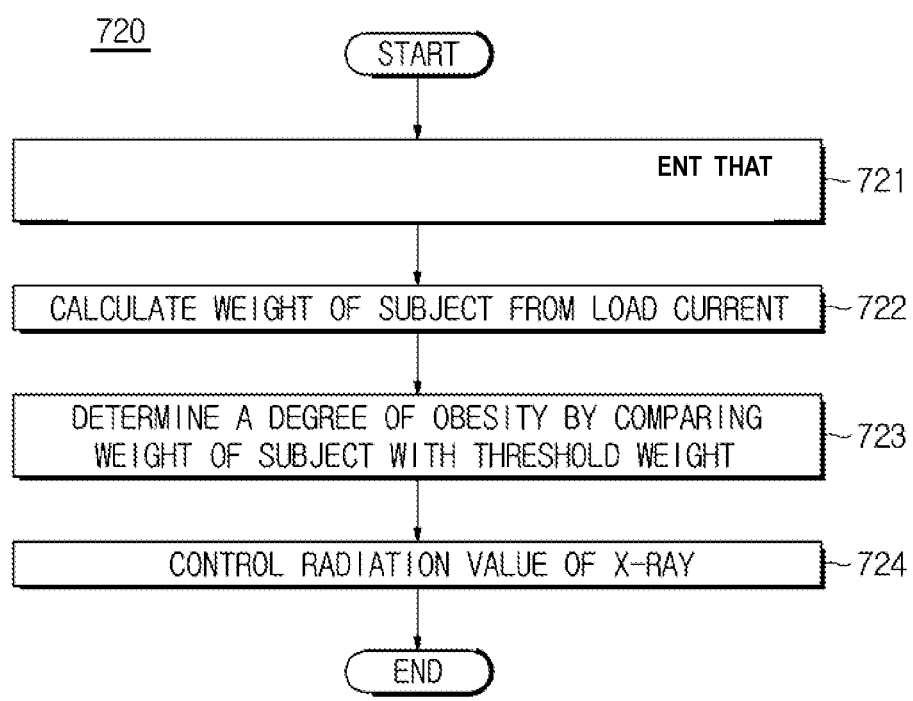
FIG. 24 is a flowchart illustrating a method for controlling an X-ray imaging apparatus, according to another embodiment of the present disclosure.

FIG. 24 is a flowchart illustrating a method for controlling an X-ray imaging apparatus, according to another embodiment of the present disclosure.

Referring to FIG. 24, the table actuator 200 drives a table motor under control of the controller 500, and measures a load current that flows through the table actuator 200 while the table motor is driven, in operation 721. Operation 721 is the same as the operation 711, thus the description of which will be omitted herein.

Next, the controller 500 calculates a weight W of the subject from the load current, in operation 722.

The controller 500 may convert the load current received into an average current form. The controller 500 calculates the weight W of the subject from the load current using the graph of relationships between weight and current as shown in FIG. 14. If the scanning table 10 is shifted upward in operation 721, the controller 500 calculates the weight W of the subject using the graph on the left of FIG. 14, or if the scanning table 10 is shifted downward in operation 721, the controller 500 calculates the weight W using the graph on the right of FIG. 14.

The controller 500 determines a degree of obesity of the subject by comparing the calculated weight W with at least one predetermined threshold weight, in operation 723.

If a single threshold weight (e.g., 130 kg) is set, the controller 500 may determine a degree of obesity of the subject by comparing the calculated weight W with the single threshold weight, and if multiple threshold weights (e.g., 130 kg, 140 kg, and 150 kg) are set, the controller 500 may determine a degree of obesity of the subject by comparing the calculated weight W with the multiple threshold weights.

Based on the determination of a degree of obesity of the subject, the controller 500 controls the intensity of the X-ray to be irradiated by the X-ray source 70, in operation 724. Operation 724 is the same as the operation 713, thus the description of which will be omitted herein.

Figure 25:
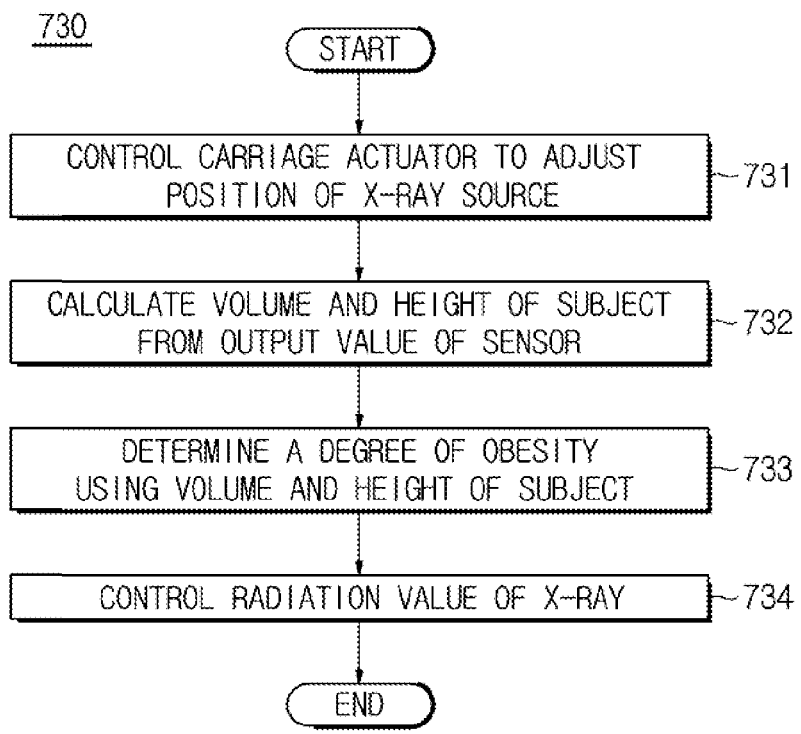
FIG. 25 is a flowchart illustrating a method for controlling an X-ray imaging apparatus, according to yet another embodiment of the present disclosure.

FIG. 25 is a flowchart illustrating a method for controlling an X-ray imaging apparatus, according to yet another embodiment of the present disclosure.

Referring to FIG. 25, the controller 500 controls the carriage actuator 110 to adjust the position of the X-ray source 70, in operation 731.

If the sensor 300 installed on the X-ray source 70 includes a proximity sensor or multiple image sensors, the controller 500 controls the carriage actuator 110 to shift the moving carriage 40 and the X-ray source 70 linked to the moving carriage in the direction of the length of the scanning table 10. While the X-ray source 70 is being shifted, an output value of the sensor 300, i.e., an output voltage of the proximity sensor or angles of the image sensors may be delivered to the controller 500.

If the sensor 300 includes a single image sensor, the controller 500 controls the carriage actuator 110 to shift the moving carriage 40 and the X-ray source linked to the moving carriage 40 to be located somewhere above the subject, and receives an output value of the sensor 300, i.e., pixel values Px of an image.

The controller 500 detects a volume and height of the subject from the output value, in operation 732.

If the controller 500 receives output voltages of the proximity sensor, the controller 500 converts the highest output voltage and the lowest output voltage to a distance to the subject and a distance to the scanning table 10, respectively, according to the upper graph of FIG. 17, and obtains the thickness (or volume V) of the abdomen of the subject to be the difference between those converted distances. Furthermore, the controller 500 may obtain the height H of the subject, exclusive of both ends that remain at the lowest output voltage in the lower graph of FIG. 17.

If the controller 500 receives pixel values Px of an image from the image sensor, the controller 500 detects the outline Po of the subject from changes in pixel values, and obtains the volume V and height H of the subject based on the detected outline Po.

If the controller 500 receives an angle of an image sensor, the controller 500 calculates a distance to the scanning table 10 or to the subject using equation 3, and obtains a difference between the greatest value and the smallest value among the calculated distances as a thickness (or volume V) of the abdomen of the subject. Furthermore, the controller 500 may obtain the height H of the subject, exclusive of both ends that remain to have the greatest value in the lower graph of FIG. 21.

The controller 500 uses the volume and height of the subject, to determine a degree of obesity of the subject, in operation 733. Based on the determination of a degree of obesity of the subject, the controller 500 controls the intensity of the X-ray to be irradiated by the X-ray source 70, in operation 734.

FIG. 26 is a flowchart illustrating a method for controlling an X-ray imaging apparatus, according to still another embodiment of the present disclosure.

Referring to FIG. 26, the table actuator 200 drives a table motor under control of the controller 500, and measures a load current that flows through the table actuator 200 while the table motor is driven, in operation 741. Next, the controller 500 calculates a weight W of the subject from the load current, in operation 742. Operations 741 and 742 correspond to the operations 721 and 722, respectively.

The controller 500 controls the carriage actuator 110 to adjust the position of the X-ray source 70, in operation 743. The controller 500 detects a volume and height of the subject from the output value of the sensor 300, in operation 744. Operations 743 and 744 correspond to the operations 731 and 732, respectively, and may come before the operation 741

The controller 500 uses the volume, height, and weight of the subject, to determine a degree of obesity of the subject, in operation 745. Based on the determination of a degree of obesity of the subject, the controller 500 controls the intensity of the X-ray to be irradiated by the X-ray source 70, in operation 746.

Several embodiments have thus been described with respect to an X-ray imaging apparatus and method for controlling the same, but it will be understood that various modifications can be made without departing the scope of the present disclosure. Thus, it will be apparent to those ordinary skilled in the art that the disclosure is not limited to the embodiments described, but can encompass not only the appended claims but the equivalents.

What is claimed is:

1. An X-ray imaging apparatus, comprising:
an X-ray source to irradiate X-rays to a subject;
a sensor mounted on the X-ray source; and
a controller to obtain a volume of the subject based on an output value of the sensor, to determine a degree of obesity of the subject based on the volume, and to control an irradiation level of the X-rays based on the degree of obesity of the subject,
wherein the output value of the sensor comprises, when the sensor comprises multiple image sensors, tilting angles of the multiple image sensors while the X-ray source is being shifted.

2. The X-ray imaging apparatus of claim 1, wherein the sensor further comprises a proximity sensor.

3. The X-ray imaging apparatus of claim 1, wherein the output value of the sensor comprises pixel values of an image captured by the multiple image sensors.

4. The X-ray imaging apparatus of claim 3, wherein the controller is configured to detect an outline of the subject from the image based on a change in pixel value and obtain a volume and height of the subject based on the outline.

5. The X-ray imaging apparatus of claim 1, further comprising: a source actuator for shifting the X-ray source.

6. The X-ray imaging apparatus of claim 5, wherein the controller is configured to control the source actuator to shift the X-ray source in the direction of a length of a scanning table, when the sensor includes one of a proximity sensor and multiple image sensors.

7. The X-ray imaging apparatus of claim 6, wherein the output value of the sensor comprises an output voltage output from the proximity sensor while the X-ray source is being shifted.

8. The X-ray imaging apparatus of claim 7, wherein the controller is configured to convert the output voltage to a distance from the proximity sensor, and to obtain a volume of the subject based on the distance.

9. The X-ray imaging apparatus of claim 8, wherein the controller is configured to obtain a first distance by converting a highest output voltage among output voltages, obtain a second distance by converting a lowest output voltage among the output voltages, and obtain a volume of the subject based on a difference between the first distance and the second distance.

10. The X-ray imaging apparatus of claim 7, wherein the controller is configured to obtain a height of the subject from a difference between a shifted distance of the X-ray source and a part of the shifted distance at which the proximity sensor outputs the lowest output voltage.

11. The X-ray imaging apparatus of claim 1, wherein the multiple image sensors each have a same focal point.

12. The X-ray imaging apparatus of claim 1, wherein the controller is configured to calculate a distance from the multiple image sensors using:

$$d = \frac{d'}{\tan(90° - \theta_1) + \tan(90° - \theta_2)}$$

where d' indicates a distance between the multiple image sensors, $\theta_1$ and $\theta_2$ indicate tilting angles of the multiple image sensors for a focal point, and d indicates a distance to the focal point from the multiple image sensors.

13. The X-ray imaging apparatus of claim 12, wherein the controller is configured to obtain a volume of the subject based on a difference between a maximum distance and a minimum distance among calculated distances.

14. The X-ray imaging apparatus of claim 12, wherein the controller is configured to obtain a height of the subject based on a difference between a shifted distance of the X-ray source and a part of the shifted distance in which the minimum distance is calculated.

15. The X-ray imaging apparatus of claim 1, wherein the irradiation level of the X-rays corresponds to one of an intensity and amount of irradiation of the X-rays.

16. An X-ray imaging apparatus, comprising:
an X-ray source to irradiate X-rays to a subject;
a table actuator to shift a scanning table; and
a controller to determine a weight of the subject based on an output value of the table actuator and to control an irradiation level of the X-rays based on the weight of the subject.

17. The X-ray imaging apparatus of claim 16, wherein the table actuator comprises at least one of a current sensor, a magnetic sensor, and a current sensing circuit.

18. The X-ray imaging apparatus of claim 17, wherein the output value of the table actuator comprises a load current that flows in the table actuator while the scanning table is being shifted in one or both of an up and down direction.

19. The X-ray imaging apparatus of claim 18, wherein the controller is configured to extract measured currents from the load current flowing in the table actuator at a sample rate, and calculate an average current from extracted measured currents using:

$$X_{rms} = \sqrt{\frac{1}{n}(X_1^2 + X_2^2 + \ldots + X_n^2)}$$

where $X_i$ (i=1, 2, . . . , n) refers to an extracted measured current, n refers to a number of extraction times, and $X_{rms}$ refers to an average current.

20. The X-ray imaging apparatus of claim 18, wherein the controller is configured to determine a degree of obesity of the subject by comparing the load current with at least one predetermined threshold current.

21. The X-ray imaging apparatus of claim 18, wherein the controller is configured to determine a weight of the subject based on the load current, and determine a degree of obesity of the subject by comparing the determined weight of the subject and at least one weight threshold.

22. An X-ray imaging apparatus, comprising:
an X-ray source to irradiate X-rays to a subject;
a sensor mounted on the X-ray source;
a table actuator to shift a scanning table; and
a controller to obtain a height of the subject based on an output value of the sensor, to obtain a weight of the subject based on an output value of the table actuator, and to control an irradiation level of the X-rays based on the height and the weight of the subject.

23. A method for controlling an X-ray imaging apparatus, the method comprising:
obtaining a volume of a subject based on an output value of a sensor mounted on an X-ray source;
determining a degree of obesity of the subject based on an obtained volume of the subject; and
controlling an irradiation level of X-rays to be irradiated by the X-ray source, based on the degree of obesity of the subject,
wherein the output value of the sensor comprises, when the sensor comprises multiple image sensors, tilting angles of the multiple image sensors while the X-ray source is being shifted.

24. A method for controlling an X-ray imaging apparatus, the method comprising:
shifting a scanning table in one of or both of an up and down direction;
determining a weight of the subject based on an output value of a table actuator while the scanning table is being shifted; and
controlling an irradiation level of X-rays to be irradiated by the X-ray source, based on the weight of the subject.

25. A method for controlling an X-ray imaging apparatus, the method comprising:

obtaining a height of a subject based on an output value of a sensor mounted on an X-ray source;

obtaining a weight of the subject based on an output value of a table actuator that shifts a scanning table; and controlling an irradiation level of X-rays to be irradiated by the X-ray source, based on the height and the weight of the subject.

* * * * *